(12) United States Patent
Wang et al.

(10) Patent No.: US 8,175,860 B2
(45) Date of Patent: May 8, 2012

(54) **METHOD OF INHIBITING THE GROWTH OF *HELICOBACTER PYLORI***

(75) Inventors: Wen-Ching Wang, Hsinchu (TW); Wen-Chi Cheng, Hsinchu (TW); Jinn-Moon Yang, Hsin-Chu (TW)

(73) Assignee: National Tsing Hua University, Hsinchu (TW)

( * ) Notice: Subject to any disclaimer, the term of this patent is extended or adjusted under 35 U.S.C. 154(b) by 279 days.

(21) Appl. No.: 12/473,155

(22) Filed: May 27, 2009

(65) Prior Publication Data

US 2010/0305152 A1  Dec. 2, 2010

(51) Int. Cl.
*G06G 7/48* (2006.01)
*G01N 33/48* (2006.01)
*G01N 31/00* (2006.01)

(52) U.S. Cl. .............................. 703/11; 702/19; 702/27

(58) Field of Classification Search ........................ None
See application file for complete search history.

(56) References Cited

OTHER PUBLICATIONS

Yang et al. "A Pharmacophore-Based Evolutionary Approach for Screening Selective Estrogen Receptor Modulators" Proteins: Structure, Function, and Bioinformatics (2005) vol. 59, pp. 205-220.*
Jai-Shin Liu et al., Structure-based inhibitor discovery of *Helicobacter pylori* dehydroquinate synthase, Biochemical and Biophysical Research Communications, 2008, pp. 1-7, vol. 373.

* cited by examiner

*Primary Examiner* — Eric S Dejong
(74) *Attorney, Agent, or Firm* — WPAT, P.C.; Anthony King

(57) ABSTRACT

A method of identifying a drug candidate to a target protein for inhibiting shikimate pathway comprising (a) performing a molecular program for computing a molecule conformation and orientation relative to an active site of the target protein and selecting top-rank molecules, (b) generating protein-molecule interacting profiles and identifying conserved interactions and pharmacophore spots, (c) developing homologous pharmacophore models for identifying pharmacophore hot spots, (d) rescoring molecules selected from step (a) by their homologous pharmacophore scores, (e) selecting potential molecules having the highest homologous pharmacophore scores, and (f) acquiring corresponding real compounds of the potential molecules selected from step (c) and identifying their inhibitory activity on the target protein by bioassay.

3 Claims, 18 Drawing Sheets

(Figure 9 continued)
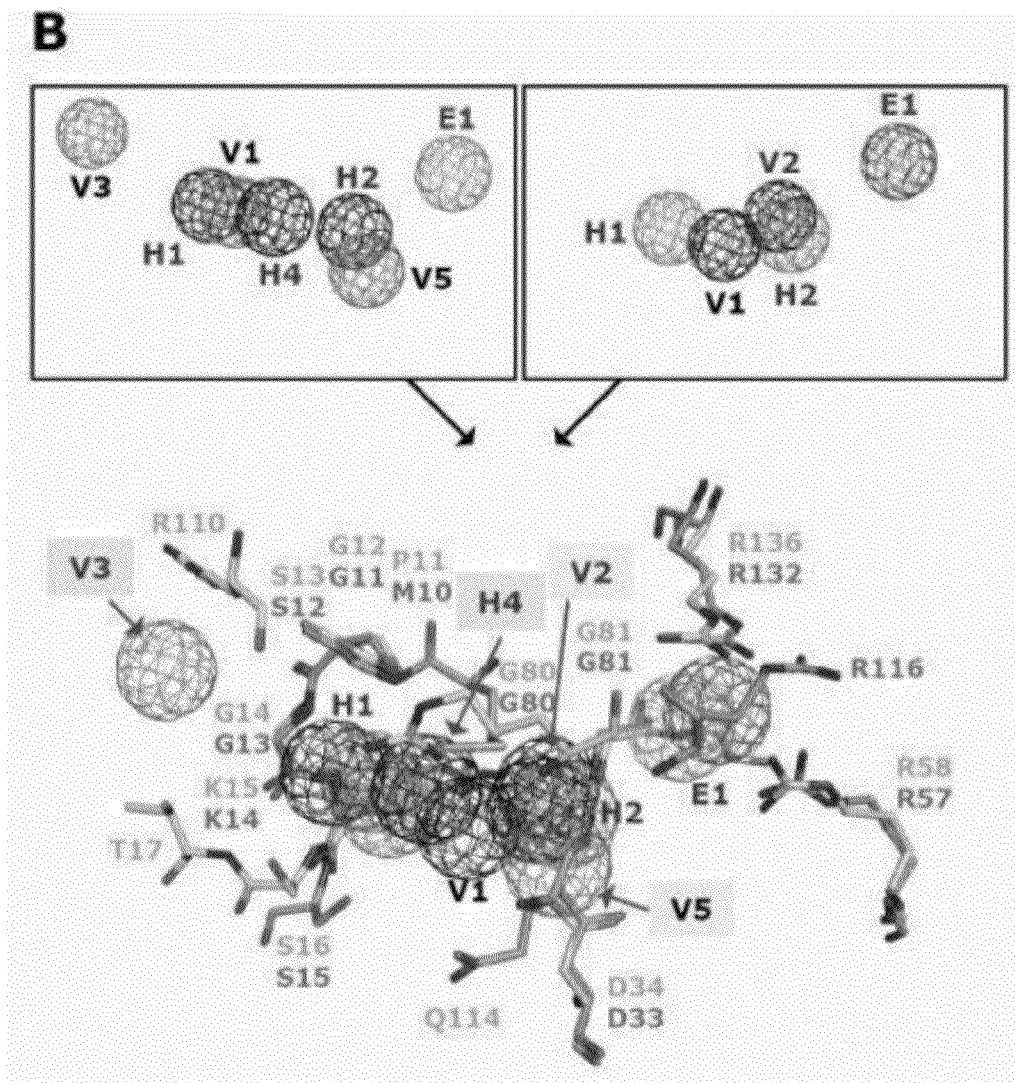

(Figure 9 continued)
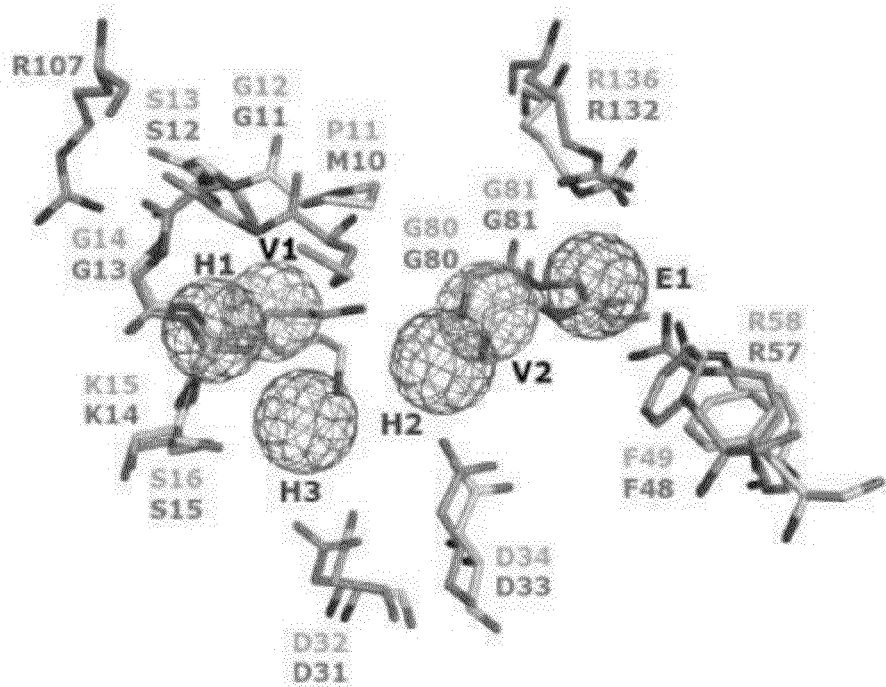
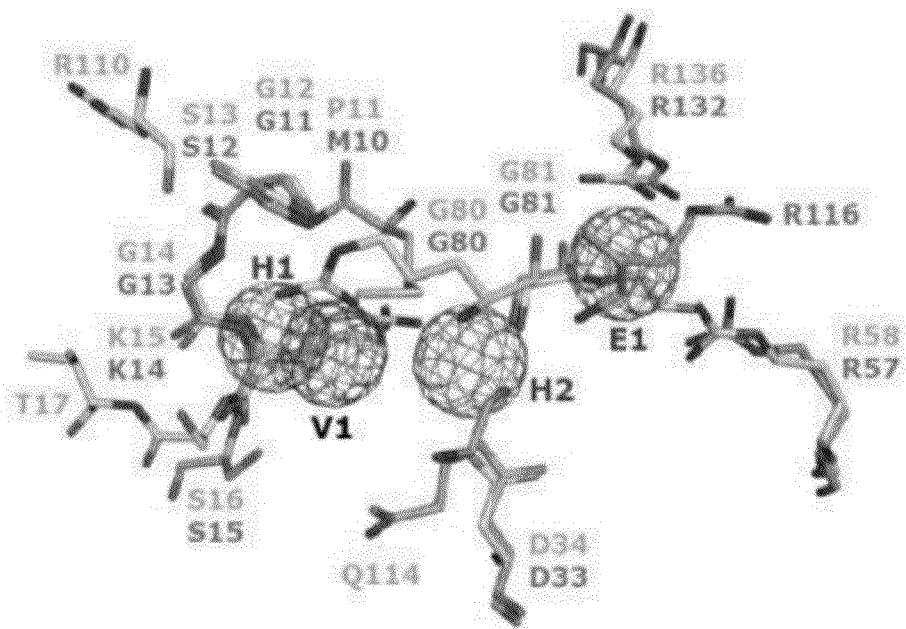

Figure 11

(Figure 12 continued)
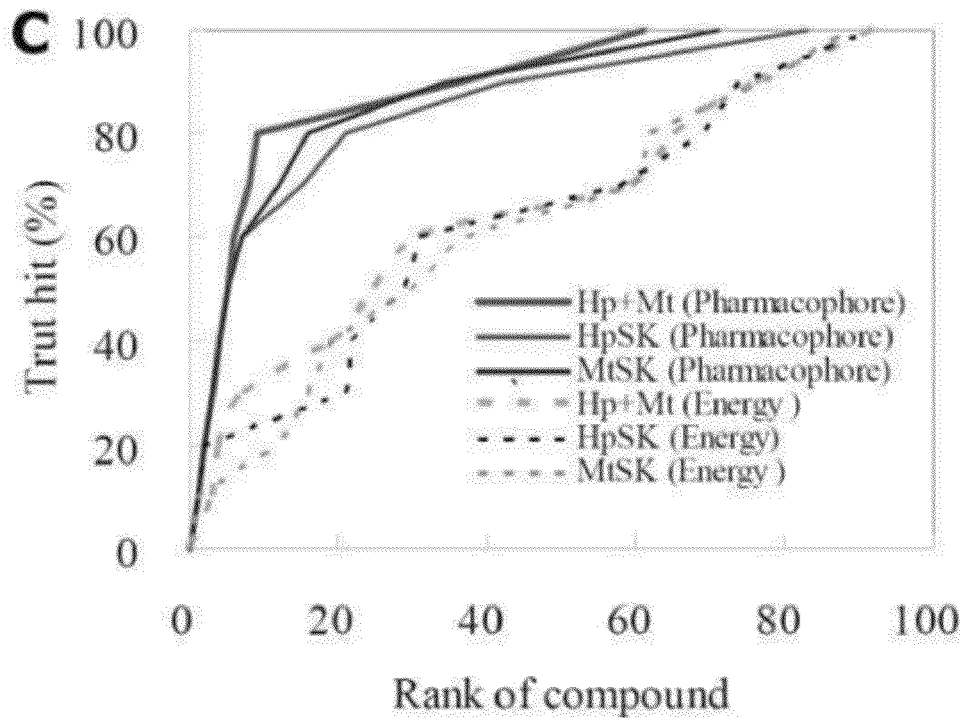
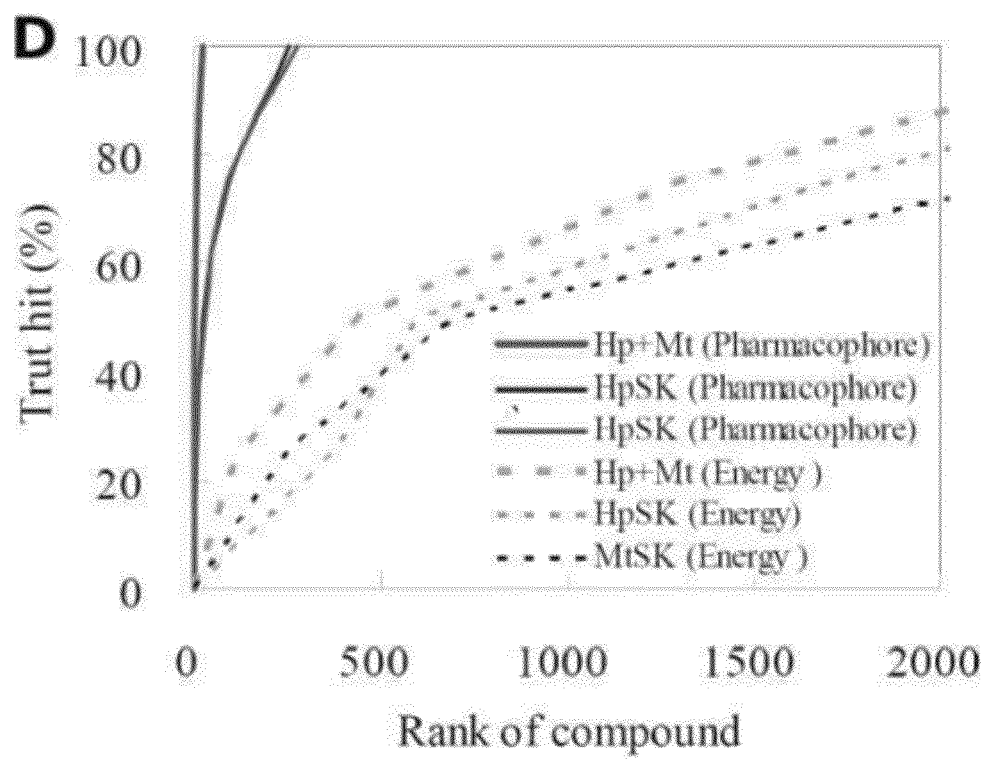

METHOD OF INHIBITING THE GROWTH OF HELICOBACTER PYLORI

FIELD OF THE INVENTION

The present invention provides a method of inhibiting the growth of plant, bacteria, fungi or parasite, which uses an inhibitor to inhibit enzymes of the shikimate pathway.

BACKGROUND OF THE INVENTION

*Helicobacter pylori*

A gram-negative spiral bacterium inhabits the gastric mucosa of humans, in which it may persist for a lifetime. The colonization of this unique ecological niche in approximately one-half of the human population makes it one of the most successful pathogens known to humankind. Enduring infection by *H. pylori* provokes active gastritis, alters gastric physiology, and may subsequently lead to peptic ulcer, atrophic gastritis, or even gastric adenocarcinoma. It is also recognized in the etiology of low-grade B-cell lymphoma.

*H. pylori* can be eradicated by the standard triple therapy comprised of a proton pump inhibitor and two antibiotic agents. The treatment of *H. pylori* infection using high-dosage antibiotics, however, has resulted in decreased efficacy. The infection proves to be difficult to cure; at least two high-dose antibiotics plus a proton pump inhibitor, twice daily for a 7- to 10-day period, is required to achieve high efficacy. Even more worrying, there is increasing emergence of resistant isolates that impede the cure rates, as seen for other bacteria including *Mycobacterium tuberculosis*. The development of novel drugs for resistant infections is thus needed for more effective control of these diseases in the future. Similarly, other resistant organisms including *Staphylococcus aureus* have become more and more difficult to cure. The need for new antibacterial therapies to overcome the problem of antibiotic resistance is therefore a major concern of healthcare professionals.

Current antibiotic agents are targeted towards a relatively small number of proteins, including cross-linking enzymes in the cell wall, ribosomal enzymes, and polymerases in DNA synthesis. One potential approach towards discovering new classes of inhibitors is to target crucial proteins in bacterial but not in mammals. The shikimate pathway, which involves seven sequential enzymatic steps in the conversion of erythrose 4-phosphate (E4P) and phosphoenolpyruvate (PEP) into chorismate for subsequent synthesis of aromatic compounds, is unique to microbial cells and parasites but absent in animals. Therefore, enzymes of this pathway are attractive targets for the development of nontoxic antimicrobial compounds, herbicides, and anti-parasitic agents. Indeed, the sixth-step enzyme, 5-enolpyruvylshikimate 3-phosphate (EPSP) synthase, has been exploited as a target with glyphosate, a well-known herbicide.

Shikimate Pathway

The shikimate pathway (shows in FIG. 1) links metabolism of carbohydrates to biosynthesis of aromatic compounds. In a sequence of seven metabolic steps, phosphoenolpyruvate and erythrose 4-phosphate are converted to chorismate, the precursor of the aromatic amino acids and many aromatic secondary metabolites. All pathway intermediates can also be considered branch point compounds that may serve as substrates for other metabolic pathways. The shikimate pathway is an attractive target for the rational drug and herbicide design because it is essential in algae, higher plants, bacteria, and fungi, but absent from mammals.

In microorganisms, the shikimate pathway is used to synthesize three proteinogenic aromatic amino acids, that is, tryptophan, phenylalanine, and tyrosine; the folate coenzimes; benzoid and naphtoid quinones; and a broad range of mostly aromatic, secondary metabolies, including some siderophores. Although the shikimate pathway branches at points, chorismate is the last common branch point for the above-mentioned compounds. Five distinct enzymes to prephenate, anthranilate, aminodeoxychorismate, isochorismate, and p-hydroxybezoate, respectively convert from chorismate. These metabolites comprise the first committed intermediates in the biosynthesis of Phe, Tyr, Trp, folate, menaquinone and the siderophore enterobactin, and ubiquinone, respectively. The synthesis of these precursors is in most cases highly regulated.

In plants, thousands of primary and secondary aromatic compounds, which play a role in plant growth, development, and defense, are synthesized via the shikimate pathway. The flow through the shikimate pathway accounts for up to 20% of the photosynthetically fixed carbon in plants, most of which is shuttled through Phe and Tyr to generate abundant phenylpropanoid metabolites. The complexes demand for aromatic secondary metabolites in specific cell types and in response to multiple environmental stimuli suggests that regulation of Phe and Tyr biosynthesis in plants may differ fundamentally from regulation observed in microorganisms.

In microorganisms, the shikimate pathway is regulated by feedback inhibition and by repression of the first enzyme 3deoxy-D-arabino-heptulosonate-7-phosphate synthase (DAHPS). In higher plants, no physiological feedback inhibitor has been identified, suggesting that pathway regulation may occur exclusively at the genetic level. This difference between microorganisms and plants is reflected in the unusually large variation in the primary structures of the respective first enzymes. Several of the pathway enzymes occur in isoenzymic forms whose expression varies with environmental condition changes and, within the plant, from organ to organ.

Knowledge of the three-dimensional structures of the enzymes will undoubtedly aid the design of useful inhibitors, which may be used as a bactericide against *M. tuberculosis*, *Xylella fastidiosa* and others. The present invention provides a new method to inhibit the growth of *H. pylori*, wherein several inhibitors works on enzymes of the shikimate pathway.

BRIEF DESCRIPTION OF THE DRAWINGS

FIG. 11 shows relations of active compounds and pharmacophore hot spots. These 10 active compounds can be roughly divided into three categories: 4 NSC compounds (orange), 3 Maybride compounds (yellow), and 2 kinase compounds (blue). The docked poses of the NSC compounds consistently occupy both ATP and shikimate sites and possess the hot spots E1 and V2. Except NSC45174, NSC compounds are competitive compounds on two sites. For the Maybride compounds, they do not have function groups to form electrostatic interactions with R57 and R132 on the hot spot E1. The docked poses of two kinase compounds located on ATP site only and they are competitive for ATP and noncompetitive for shikimate.

SUMMARY OF THE INVENTION

Figure 1:
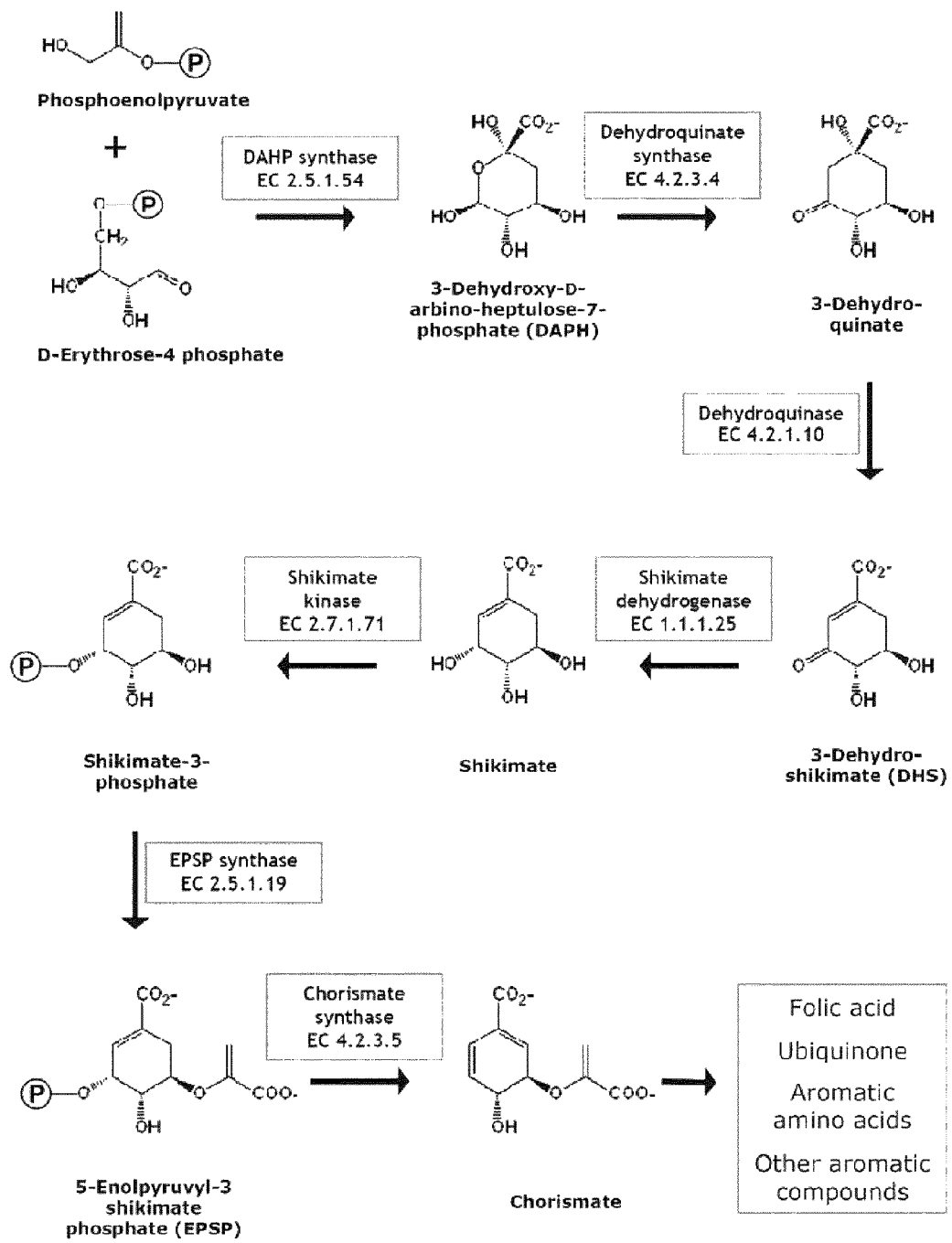
FIG. 1 shows the shikimate pathway.

The present invention relates to a method of inhibiting the growth of plant, bacteria, fungi or parasite of a subject comprising administrating to the subject an effective amount of a compound selected from the group consisting of 2-(1,3-benzothiazol-2-ylsulfanyl)-N-(3-cyano-6-methyl-4,5,6,7-tetrahydro-1-benzo-thiophen-2-yl)acetamide, 2-amino-4-methylsulfanyl-6-[2-(3-nitrophenyl)-2-oxo-ethyl]sulfanylpyridine-3,5-dicarbonitrile, 4-(5-nitro-1,3-dioxo-1H-benzo[de]iso-quinolin-2(3H)-yl)-N-(4-(trifluoromethyl)phenyl)benzenesulfonamide, N'-(3-nitro-benzoyl)-9H-xanthene-9-carbohydrazide, N'-(3-fluorobenzoyl)-9H-xanthene-9-carbohydrazide, (Z)-4-(3,5-dichlorophenoxy)-N'-hydroxy-3-nitrobenzimidamide, 7,7'-carbonylbis(azanediyl)bis(4-hydroxynaphthalene-2-sulfonate), 5-((E)-(4-((E)-(4-((E)-(2,4-diamino-5-methylphenyl)diazenyl)-3-methyl-2-sulfonatophenyl)diaze-nyl)phenyl)diazenyl)-2-hydroxybenzoate, 5-((E)-(4-((E)-(2-benzyl-8-hydroxy-6-sulfonatonaphthalen-1-yl)diazenyl)phenyl)diazenyl)-2-hydroxybenzoate, (E)-7-amino-4-hydroxy-3-((5-hydroxy-7-sulfonatonaphthalen-2-yl)diazenyl)naphthalene-2-sulfonate, (Z)-2-(3,4-dihydroxybenzoyl)-3-(3,4-dihydroxyphenyl)acrylonitrile, and (Z)-3-(3,5-dibromo-4-hydroxybenzylidene)-5-iodoindolin-2-one.

Detailed Description of the Invention

The present invention provides a method of inhibiting the growth of bacteria or fungi of a subject comprising administrating to the subject an effective amount of a compound selected from the group consisting of

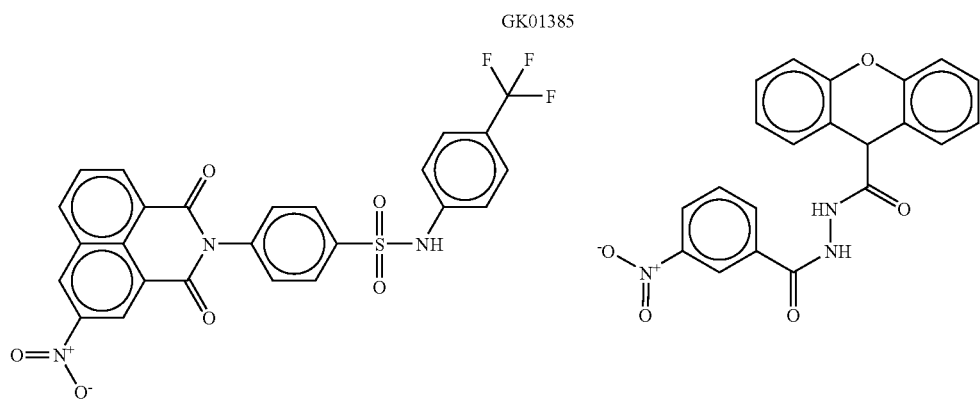
(the supplier catalog number)
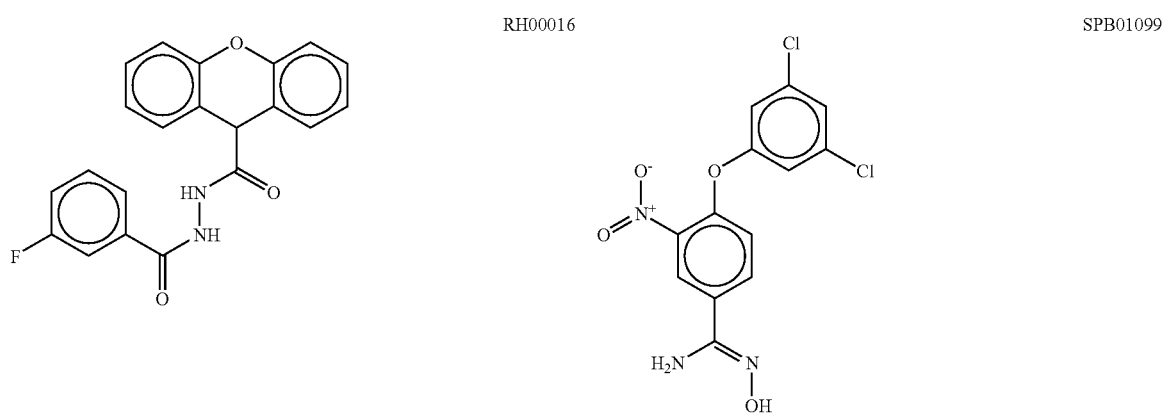
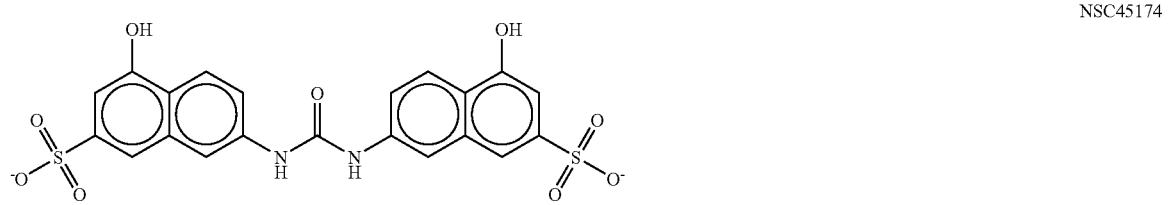
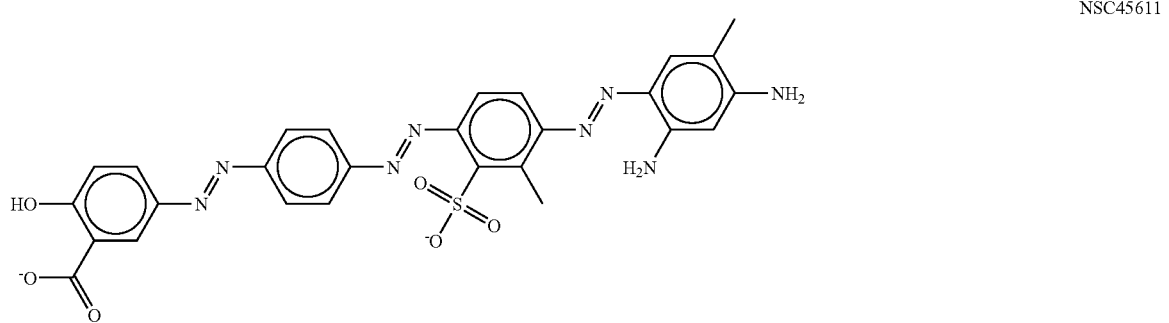

NSC45612

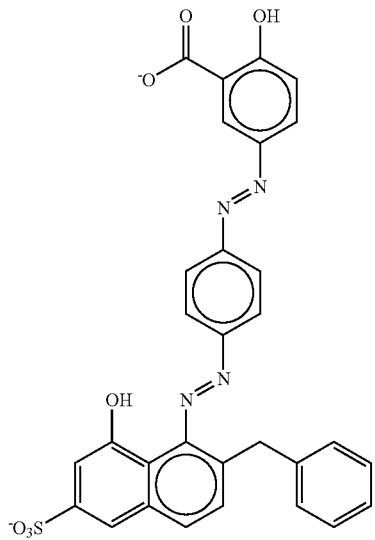

NSC162535

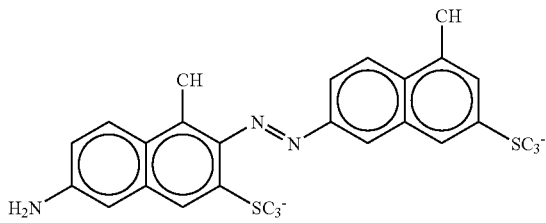

AG538

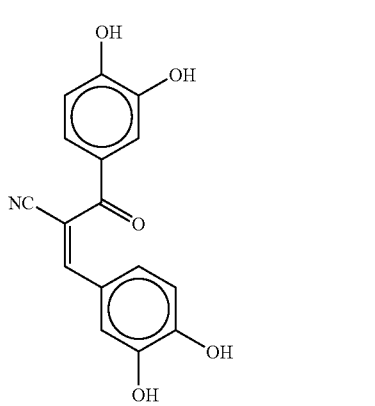

GW5074

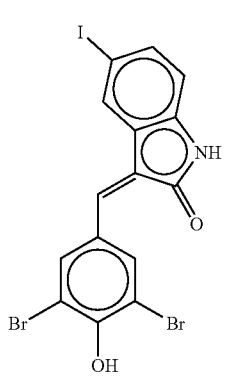

HTS11955

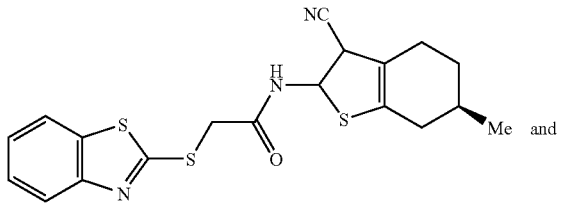

RH00573

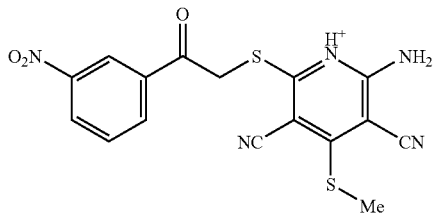

wherein several compounds works on enzymes of the shikimate pathway. In a preferred embodiment, the method of the present invention is used to inhibit the growth of *H. pylori* or *M. tuberculosis*.

The method of the present invention provides several enzyme inhibitors of the shikimate pathway The targeted enzymes in the shikimate pathway are showed as follows.

Dehydroquinate Synthase (DHQS)

The second enzyme of the pathway, is the second-step enzyme of the shikimate pathway and catalyzes the conversion of 3-deoxy-Darabino-heptulosonate 7-phosphate (DAHP) into 3-dehydroquinate (DHQ). In an animal model, infection with a knock-out DHQS *Salmonella typhimurium* mutant revealed attenuation in the virulence, which supports that DHQS is a potential drug target. The first structure of DHQS from a microbial eukaryote *Aspergillus nidulans* (AnDHQS) is that of a homodimer. Each subunit consists of an N-terminal Rossmann-fold domain and a C-terminal a-helical domain. The substrate analog carbaphosphonate (CBP), $Zn^{2+}$, and a cofactor $NAD^+$ are located in a deep cleft between the N and C domains. Structures of other liganded AnDHQS complexes (various combinations of NAD, ADP and CBP) suggest a large-scale open-to-closed induced-fit movement of the enzyme upon substrate-binding, enabling the catalytic reaction to take place.

Shikimate Kinase

The fifth enzyme of the pathway, catalyzes the specific phosphorylation of the 3-hydroxyl group of shikimic acid using ATP as a cofactor. In *Escherichia coli*, the shikimate kinase reaction is catalyzed by two isoforms that share 30% sequence identity: shikimate kinase I, encoded by the aroK gene, and shikimate kinase II, encoded by the aroL gene. Most bacteria, however, have only one shikimate kinase. The first structure of shikimate kinase from *Erwinia chrysanthemi*

(EcSK) demonstrates an alpha/beta protein with a central sheet of five parallel beta strands flanked by alpha helices, structurally belonging to the nucleoside monophosphate (NMP) kinase family. The determined apo EcSK and EcSK-MgADP complex structures reveal an open-to-closed induced-fit movement of the enzyme upon substrate binding, as also observed in NMP kinases such as adenylate kinase. Other determined shikimate kinase structures include *E. coli* shikimate kinase I, *Campylobacter jejuni* shikimate kinase (CjSK), *M. tuberculosis* shikimate kinase (MtSK), the MtSK-MgADP complex, and the ternary MtSK-MgADP-shikimate complex.

In the method of the present invention, the inhibitors of the dehydroquinate synthase of the shikimate pathway are 2-(1,3-benzothiazol-2-ylsulfanyl)-N-(3-cyano-6-methyl-4,5,6,7-tetrahydro-1-benzo-thiophen-2-yl)acetamide and 2-amino-4-methylsulfanyl-6-[2-(3-nitrophenyl)-2-oxoethyl]sulfanylpyridine-3,5-dicarbonitrile.

In the method of the present invention, the inhibitors of the shikimate kinase of the shikimate pathway are 4-(5-nitro-1,3-dioxo-1H-benzo[de]isoquinolin-2(3H)-yl)-N-(4-(trifluoromethyl)phenyl)benzenesulfonamide, N'-(3-nitrobenzoyl)-9H-xanthene-9-carbohydrazide, N'-(3-fluorobenzoyl)-9H-xanthene-9-carbohydrazide, (Z)-4-(3,5-dichlorophenoxy)-N'-hydroxy-3-nitrobenzimidamide, 7,7'-carbonylbis(azanediyl)bis(4-hydroxynaphthalene-2-sulfonate), 5-((E)-(4-((E)-(4-((E)-(2,4-diamino-5-methylphenyl)diazenyl)-3-methyl-2-sulfonato-phenyl)diazenyl)phenyl)diazenyl)-2-hydroxybenzoate, 5-((E)-(4-((E)-(2-benzyl-8-hydroxy-6-sulfonatonaphthalen-1-yl)diazenyl)phenyl)dia-zenyl)-2-hydroxybenzoate, (E)-7-amino-4-hydroxy-3-((5-hydroxy-7-sulfonatonaphthalen-2-yl)diazenyl)naphtha-lene-2-sulfonate, (Z)-2-(3,4-dihydroxybenzoyl)-3-(3,4-dihydroxyphenyl)acrylonitrile, and (Z)-3-(3,5-dibromo-4-hydroxybenzylidene)-5-iodoindolin-2-one.

The present invention also provides a method of identifying a drug candidate to a target protein, comprising:
(a) performing a molecular docking program for computing a molecule comformation and orientation relative to an active site of the target protein and selecting top-rank molecules of docked poses generated by the program,
(b) generating protein-molecule interacting profiles of the molecules selected from step (a) and identifying conserved interactions and pharmacophore hot spots,
(c) developing homologous pharmacophore models from the interacting profiles of step (b) for identifying consensus hot spots by superimposing multiple pharmacophore spots,
(d) rescoring molecules selected from step (a) by both energy-based and homologous pharmacophore methods,
(e) selecting potential molecules which have the highest scores from the score fitness function based on the apo-form and closed homologous pharmacophore models, and
(f) identifying inhibition of target protein activity of the potential molecules selected from step (e) by bioassay In a preferred embodiment, the protein-molecule interacting profiles in step (b) comprises hydrogen-bonding interactions, electrostatic interactions and VDW interactions; the molecular docking program of step (a) is GEMDOCK; and the bioassay of step (f) is enzyme activity assay.

In a more preferred embodiment, the method of identifying a drug candidate to a target protein further comprises a step (g) after step (f), wherein the step (g) is to evaluate performance of the homologous pharmacophore models of step (c) using active and inactive molecules from bioasssay of step (f), and refine hot spots of the homologous pharmacophore models.

EXAMPLES

The examples below are non-limiting and are merely representative of various aspects and features of the present invention.

Example 1

Example 1 was the inhibitor screening of dehydroquinate synthase of *H. pylori* (HpDHQS), which presented the crystal structure of HpDHQS in complex with NAD. Despite a low sequence identity, HpDHQS structure showed a homologous DHQS fold. Structural analysis reveals that the binary complex was present in an open-form conformation and contains conserved substrate-binding residues. Structure-based approach was subsequently employed to identify inhibitors with $IC_{50}$ values in the micromolar range.

Materials and Methods

Protein Expression and Purification

The aroB gene encoding HpDHQS was amplified from *H. pylori* 26695 genomic DNA by PCR and inserted into the pQE30 expression vector. The HpDHQS protein was expressed from *E. coli* JM109 cells transformed with pQE30-HpDHQS. The expressed HpDHQS protein was purified by immobilized nickel-ion chromatography.

Preparation of DAHP

3-Deoxy-D-arabino-heptulosonate 7-phosphate (DAHP) was prepared by the enzymatic condensation of D-erythrose 4-phosphate (E4P) and phosphoenolpyruvate (PEP) catalyzed by *Corynebacterium glutamicum* DHAP synthase. The recombinant *C. glutamicum* DHAP synthase was expressed and purified as previously described. The standard reaction mixture (1.0 ml) consisted of 100 μM PEP, 100 μM E4P, 100 μM cobalt chloride in 50 mM Bis-Tris propane buffer (pH 7.4), and 39 nM of the purified *C. glutamicum* DHAP synthase. A spectrophotometric method was utilized to detect the level of the PEP conversion at 232 nm ($\epsilon$=2800 $M^{-1}$ $cm^{-1}$). The mixture was passed through a column of Dowex 1X8 and DAHP was eluted with 0.6 M HCl.

Enzymatic Assay

The level of DAHP was determined by a thiobarbiturate assay method. All assays were conducted at 37° C. in a 200-μl solution containing 20 mM Bis-Tris propane buffer (pH 7.0), 0.5 mM DAHP, 0.02 mM cobalt chloride, 0.02 mM $NAD^+$ and 1 μM HpDHQS. The residual DAHP was oxidized by per-iodate to produce formylpyruvate, which then reacted with thiobarbiturate to yield a pink adduct, and this chromophore was monitored at A549 after extraction into cyclohexanone.

Inhibition Assay

Compounds were prepared to 100 mM in dimethylsulfoxide (DMSO) solutions. A 5% DMSO control was included for each set of measurements. About 1 μM HpDHQS was added to the mixture containing the compound to be tested with the standard assay mixture. The test compounds were also evaluated whether they interfered the thiobarbiturate assay system in the absence of HpDHQS. The initial velocities were plotted against the inhibitor concentrations to obtain the $IC_{50}$ by using the following equation $A[I]=A[0]\times\{1-([I]/[I]+IC_{50})]\}$ wherein A[I] was the enzyme activity with inhibitor concentration [I], and A[0] was the enzyme activity without the inhibitor.

Crystallization

Crystallization was performed by the hanging-drop vapor-diffusion method at 20° C. using the protein solution (~10 mg/ml) in 50 mM Tris-HCl, pH 8.0. The best crystals were obtained in a solution containing 20 mM NAD, 3.5 M NaFormate, 0.1 M Tris-HCl (pH 7.5). The crystals grew in a cubic form with a maximum size of about 0.3×0.3×0.3 mm within 7 days.

Data Collection and Structure Determination

The crystals belong to space group R3 with cell dimensions of a=158.29 Å, b=158.29 Å, and c=97.38 Å, and contain a dimer in the asymmetric unit. Diffraction data were collected at the Macromolecular X-ray Crystallographic Laboratory of National Tsing Hua University, Hsinchu, Taiwan and processed with the HKL suite. All data-sets were collected at −150° C. and Fomblin was used as cryoprotectant. The HpDHQS structure was solved by molecular replacement with the program AMoRe, using the AnDHQS•NAD structure (PDB code, INRX) as the search template. Rotation and translation functions followed by the rigid body refinement procedure were carried out using data from 8-to 3-Å resolution. Crystallographic refinement was carried out using REFMAC5 program and coupled to ARP/wARP. Omit density maps were produced and inspected after refinement to revise the model manually with the program O. The overall quality of the final model was assessed by the program PROCHECK.

Structural Comparisons

Structure comparisons with AnDHQS•NAD (PDB code, INRX), AnDHQS•NAD•CBP (PDB code, 1DQS), SaDHQS•NAD (PDB code, 1XAH), SaDHQS•NAD•CBP (PDB code, 1XAJ) and TtDHQS (PDB code, 1UJN) were carried out using the program LSQMAN in O to superimpose Cα atoms. Combined sequence and secondary structure alignments and figure preparation were done with the program ESPript. Structural figures were prepared with the program PyMOL (www.pymol.org).

Virtual Screening

The HpDHQS•NAD•CBP model was prepared using the AnDHQS•NAD•CBP structure (PDB code, 1DQS) as the template model. The sequence alignment was performed using the ClustalW program and was manually optimized to match the secondary elements of the conserved N and C domains. Homology module implemented in InsightII software package (Accelrys, San Diego, Calif.) was used to generate the closed HpDHQS model. MODELLER was then conducted to build 10 full-atoms, in which the best geometry-quality model was selected using PROCHECK. NAD and CBP were sequentially docked into this model using the program GOLD version 2.1 (CCDC Software Limited, Cambridge, U.K.). The NAD site was defined within a 20-Å radius around the N atom of G95 and the CBP site was within a 10-Å radius around the Ne atom of K132. Standard default parameter settings were used. The three best solutions were obtained until a root mean square deviation (rmsd) tolerance of 1.5 Å. This ternary complex model was subjected to energy minimization using the CHARMm force field with InsightII package (Version 2005). This was done by the steepest descent minimization and the conjugate gradient minimization until an rmsd of 0.05 Å. Anolea and Verify3D were used to assess the overall protein quality of the final model. The Maybridge database that contains 59284 compounds was utilized. The 2D compounds in SDF format were converted into 3D structures by CONCORD module of Sybyl program (Version 7.1, Tripos Inc., St. Louis, Mo.). Docking of small molecules into the HpDHQS model was conducted with GOLD version 2.1 and GEMDOCK. The automatic searching efficiency was set at 200% along with other default parameters to increase the search efficiency. Twenty genetic algorithm (GA) runs were carried out for each compound.

Results

Structure Determination and Overall Structure Description

Despite a number of crystal forms, only one crystal form that was obtained in a solution containing 20 mM NAD diffracted to a high resolution (2.4 Å). The structure was determined by the molecular replacement method using the AnDHQS•NAD structure as the template. Finally, the model was refined to 2.4-Å resolution with an R and Rfree of 20.7% and 25.7%, respectively.

Figure 2:
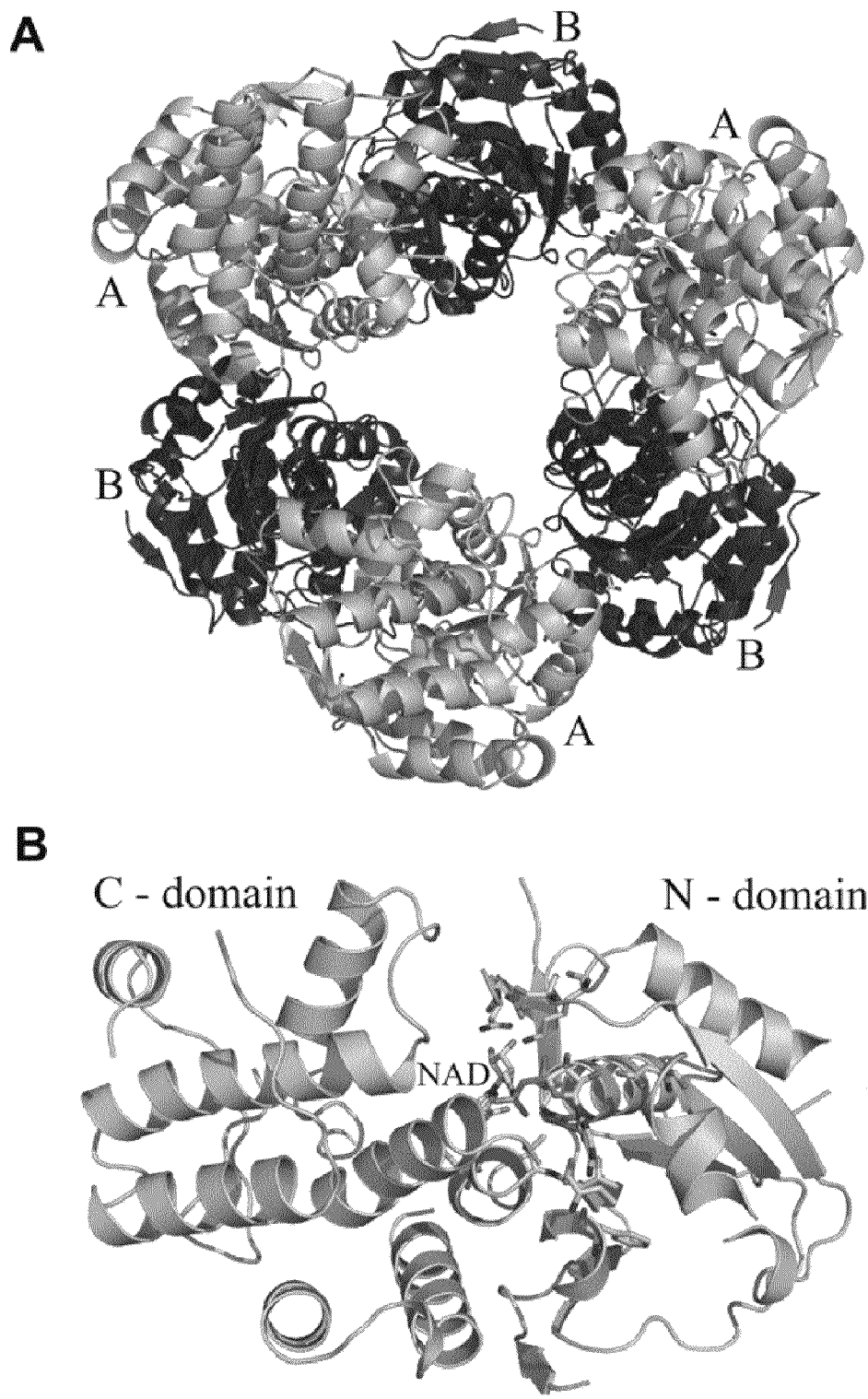
FIG. 2 shows the structures of the dehydroquinate synthase of *H. pylori* (HpDHQS). (A) The ribbon representation of hexameric structure (AB)$_3$ viewed down a threefold axis. Three A subunits are depicted in green and the three B subunits are in red. (B) HpDHQS is shown in ribbon model. Each subunit consists of an NAD situated in the cleft between N and C domains. G94 and G95 are shown as magenta.

The electron density map of HpDHQS revealed two molecules (AB) per asymmetric unit. Disordered regions that could not be defined include the N-terminal 1-3 segment and two loop regions (215-223 and 292-314). The electron density map showed the presence of a piece of density in each subunit, which could be modeled as a zinc ion in each subunit. Subunits A and B associate into an AB dimer related by a non-crystallographic twofold axis, and three AB dimers assemble into a hexamer along the 3-fold axis (shown as FIG. 2A).

Figure 3:
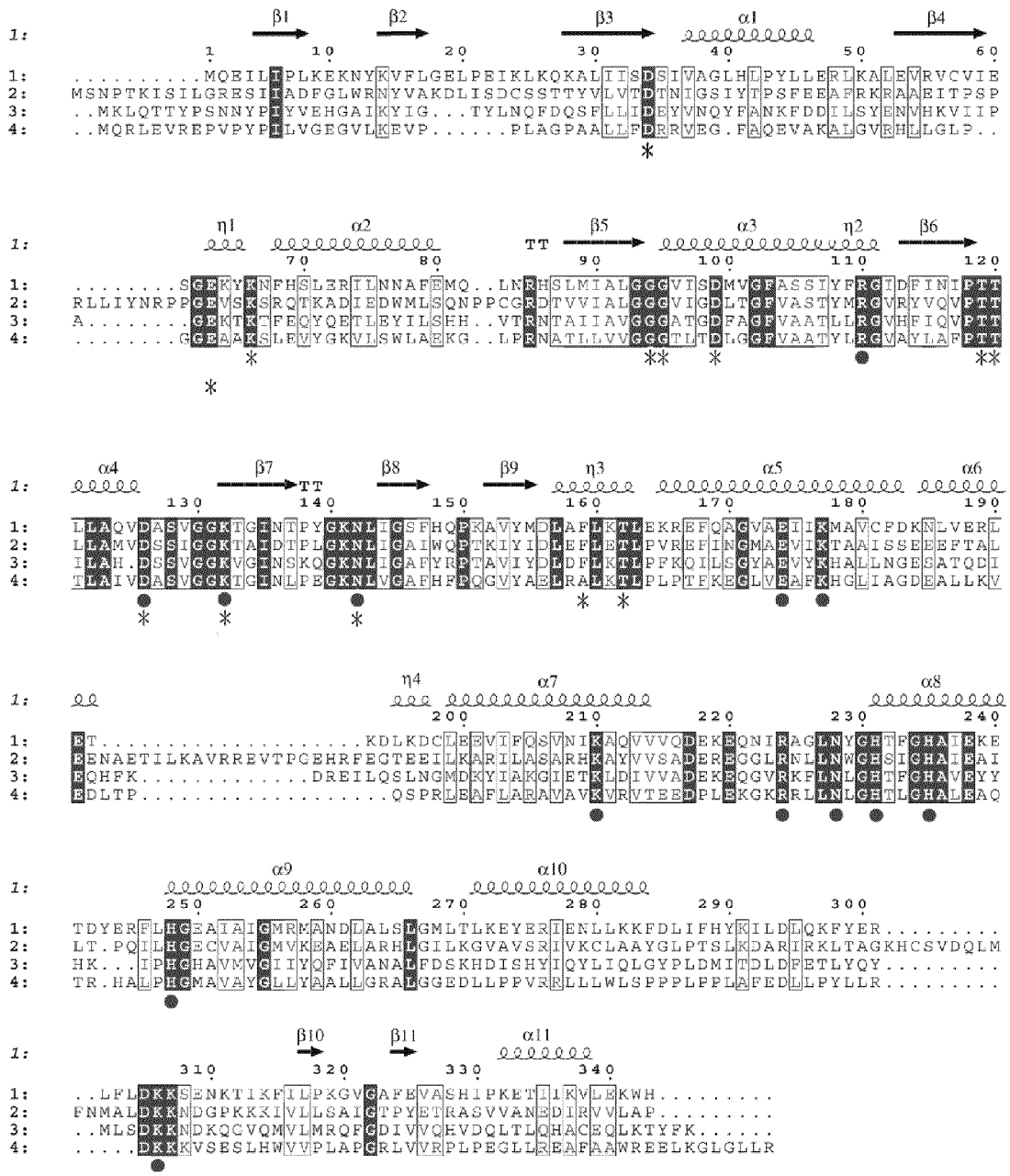
FIG. 3 is the structure-based alignments of 3-dehydroquinate synthases. Number 1 is *H. pylori* 3-dehydroquinate synthase; Number 2 is *Aspegillus nidulans* 3-dehydroquinate synthase; Number 3 is *Staphylococcus aureus* 3-ehydroquinate synthase; Number 4 is *Thermus thermophilus* 3-dehydroquinate synthase; the secondary structural elements are shown above the sequence. NAD-binding residues are indicated as black asterisks. Conserved residues involved in catalysis are indicated as solid circles.

Each subunit consisted of two domains that were characteristic of other DHQS members (shown as FIG. 2B): (i) the N domain, which had the Rossmann-type architecture, and (ii) the C domain, which contained an α-helical structure. Superimposition of chain A and chain B revealed the essentially overlapping structures (rmsd of Cα atoms=0.731 Å]. NAD of each subunit was present in the deep cleft, analogous to those observed in other binary structures. The conserved G94 and G95 in the P-loop region made hydrogen-bonding contacts with the phosphate moiety of NAD. Other NAD-binding residues included D34, E63, K66, D99, T119, T120, D126, K132, N142, and T162, which were strictly conserved among DHQSs (shown as FIG. 3).

Structural Comparison

From on analysis using DALI, the HpDHQS structure was found to share structural homology with structures of DHQSs. Superimposition with various DHQS structures also revealed modest rmsd values of the overall Cα atoms (1.1 -1.6 Å').

As had been described in various liganded AnDHQS and SaDHQS structures, a structural transition from an open to a close state was most likely to take place upon binding to CBP owing to the closure between the N and C domains (differences in domain orientations: AnDHQS, 11-13°; SaDHQS, 8°). Thus, comparing the domain orientation between the HpDHQS•NAD structure and other DHQS structures, calculating the rigid-body rotational angle required for the superimposition of the C domains after the primary superimposition at the N domains. Among different DHQSs, the AnDHQS•NAD complex (open form) showed the least difference (1.8°) in domain orientation as compared with 14.4° for the AnDHQS•NAD•CBP complex (closed form). These results suggested that the HpDHQS•NAD structure was also present as an open form, as reported for the TtDHQS structure.

Figure 4:
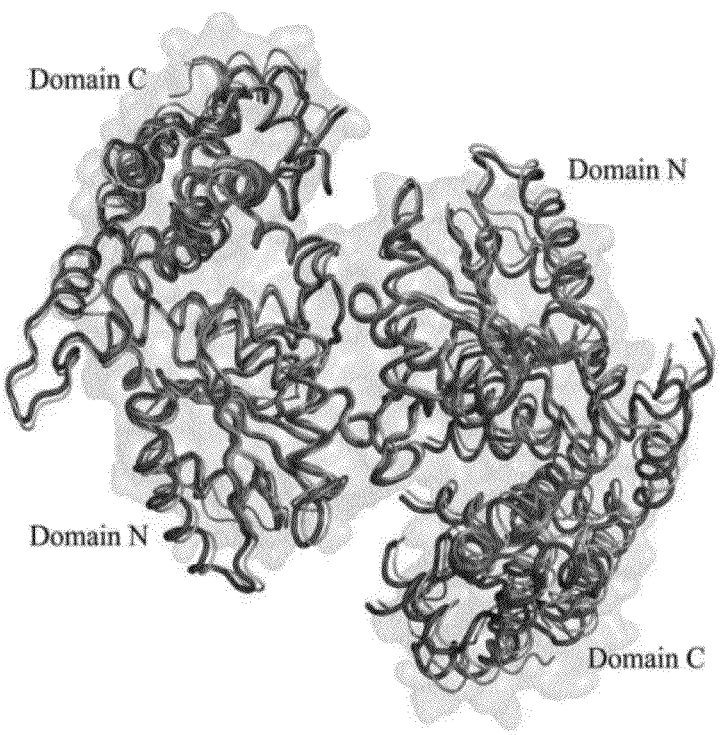
FIG. 4A shows the superposition of three dimeric DHQSs, HpDHQS•NAD, AnDHQS•NAD and AnDHQS•NAD•CBP. HpDHQS•NAD (dark green) and AnDHQS•NAD (pink) are shown as thin ribbon models and AnDHQS•NAD•CBP (red) are shown as a thick ribbon model.
FIG. 4B shows stereoview of the active site in the open form DHQSs. Residues in HpDHQS (green) are shown as heavy sticks and those in AnDHQS (magenta), SaDHQS (cyan) and TtDHQS (orange) are shown as thin sticks.
Figure 4:
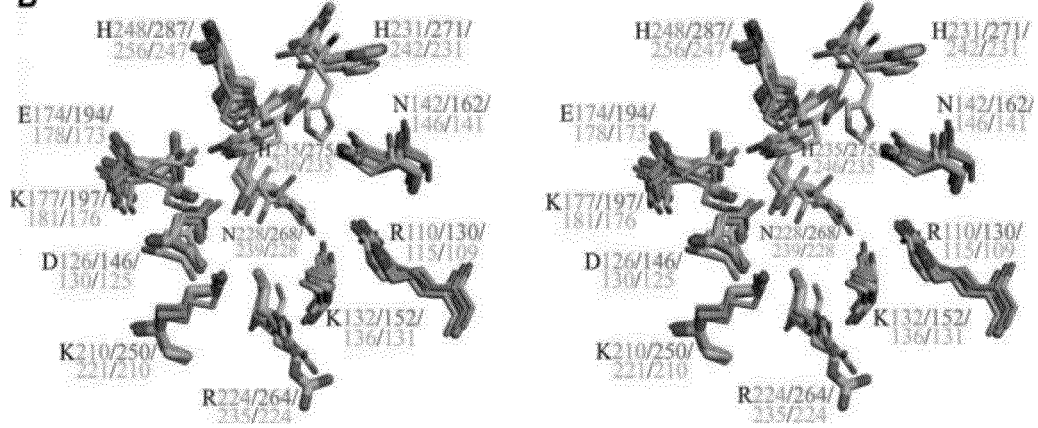

Analysis of dimeric interactions among various DHQS structures revealed that buried residues involved in the formation of the dimer were from the N domain (α2, α3, γ2, β7 and β8). Approximately similar subunit surface areas were used for the formation of the dimer. Notably, a strictly conserved arginine (R110) hydrogen bonded with the peptide O atom (T133) from the neighbor subunit. Based on the optimized alignment of the N domain in the A subunit, superimposition of dimers revealed that the dimeric N domains (corresponding to residues 4-163 in HpDHQS) were well superimposed among HpDHQS•NAD (open), AnDHQS•NAD (open) and AnDHQS•NAD•CBP (close) (rmsd in the Cα atoms: HpDHQS•NAD vs. AnDHQS•NAD, 0.66 Å; HpDHQS•NAD vs. AnDHQS•NAD•CBP: 0.67 Å) (shown as FIG. 4A). As expected, there was a large difference in the domain orientation between the open and close forms for each monomer (shown as FIG. 4A). The superimposed C domains exhibited higher deviation in the Cα atom positions (rmsd in the Cα atoms corresponding to residues 164-343 in HpDHQS: HpDHQS•NAD vs. AnDHQS•NAD, 1.20 Å; HpDHQS•NAD vs. AnDHQS•NAD•CBP, 2.05 Å). These results suggested that the N domain contributed to the formation of a closely associated dimer, which helped to maintain the minimal translational mobility of nearby fine-tuned catalytic residues for efficient catalysis.

Next, comparing crucial residues in the binding pockets, residues that were responsible for the conversion of DAHP to dehydroquinate in AnDHQS were conserved among DHQSs. Superimposition of open form DHQS structures showed the virtually identical Cα conformation of these residues in the binding pocket located between the N and C domains (shown as FIG. 4B). Side chains of two residues that corresponded to H235 and R224 in HpDHQS were noted as displaying higher deviation. In the presence of CBP, they interacted with CBP and were superimposed relatively well between the bound structures (SaDHQS•NAD•CBP and AnDHQS•NAD•CBP structures). These results together suggested a conserved binding pocket among DHQSs.

Inhibitor Screening

Given the conserved binding pocket among DHQSs, next step was seeking to utilize a structure-based approach to search for possible potent inhibitors. The CBP-bound HpDHQS closed model was built using the closed AnDHQS•NAD•CBP structure as the template model. Superimposition analysis between the HpDHQS•NAD and HpDHQS•NAD•CBP models revealed that either N or C superimposed domains had limited conformational change (rmsd of Cα atoms for the N domains=0.08 Å; rmsd of Cα atoms for the C domains=0.65 Å), respectively. The large difference was seen in domain orientation (14.0°), hence supporting that the ternary complex model was a closed form.

Using this model to performed virtual screening over the Maybridge database. The docked molecules were ranked by the GOLDScore fitness function and the best 100 molecules were selected. The top ranking compounds that were commercially available were then purchased for inhibitory assay. Seven showed inhibitory action at 500 µM. The two best inhibitors, HTS11955 (2-(1,3-benzothiazol-2-ylsulfanyl)-N-(3-cyano-6-methyl-4,5,6,7-tetrahydro-1-benzothiophen-2-yl)acetamide) and RH00573 (2-amino-4-methylsulfanyl-6-[2-(3-nitrophenyl)-2-oxoethyl]sulfanylpyridine-3,5-dicarbonitrile), had $IC_{50}$ values of 61.0 and 84.4 µM, respectively (Table 1).

TABLE 1

Supplier catalog number and IUPAC (International Union of Pure and Applied Chemistry) name of the inhibitors of shikimate pathway in the method of the present invention.

| | Supplier catalog number | Chemical Name |
|---|---|---|
| Inhibitors of shikimate kinase | GK01385 | 4-(5-nitro-1,3-dioxo-1H-benzo[de]isoquinolin-2(3H)-yl)-N-(4-(trifluoromethyl)phenyl)benzenesulfonamide |
| | RH00037 | N'-(3-nitrobenzoyl)-9H-xanthene-9-carbohydrazide |
| | RH00016 | N'-(3-fluorobenzoyl)-9H-xanthene-9-carbohydrazide |
| | SPB01099 | (Z)-4-(3,5-dichlorophenoxy)-N'-hydroxy-3-nitrobenzimida-mide |
| | AG538 (IGF-1 receptor kinase inhibitor) | (Z)-2-(3,4-dihydroxybenzoyl)-3-(3,4-dihydroxyphenyl)acrylonitrile |
| | GW5074 | (Z)-3-(3,5-dibromo-4-hydroxybenzylidene)-5-iodoindolin-2-one |
| | NSC45612 | 5-((E)-(4-((E)-(2-benzyl-8-hydroxy-6-sulfonatonaphthalen-1-yl)diazenyl)phenyl)diazenyl)-2-hydroxybenzoate |
| | NSC162535 | (E)-7-amino-4-hydroxy-3-((5-hydroxy-7-sulfonatonaphthalen-2-yl)diazenyl)naphthalene-2-sulfonate |
| Inhibitors of shikimate kinase | NSC45174 | 7,7'-carbonylbis(azanediyl)bis(4-hydroxynaphthalene-2-sulfonate) |
| | NSC45611 | 5-((E)-(4-((E)-(4-((E)-(2,4-diamino-5-methylphenyl)diazenyl)-3-methyl-2-sulfonatophenyl)diazenyl)phenyl)diazenyl)-2-hydroxybenzoate |
| Inhibitors of dehydroquinate synthase (DHQS) | HTS11955 | 2-(1,3-benzothiazol-2-ylsulfanyl)-N-(3-cyano-6-methyl-4,5,6,7-tetrahydro-1-benzothiophen-2-yl)acetamide |
| | RH00573 | 2-amino-4-methylsulfanyl-6-[2-(3-nitrophenyl)-2-oxoethyl]sulfanylpyridine-3,5-dicarbonitrile |

Figure 5:
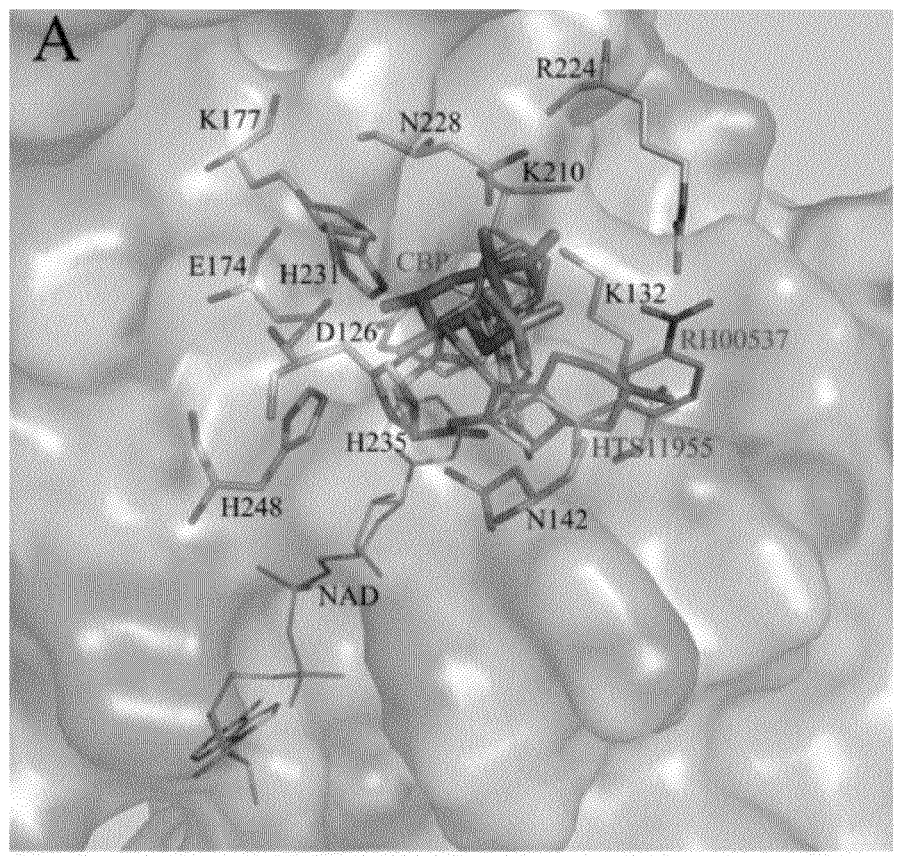
FIG. 5A shows the molecular surface of HpDHQS with inhibitors. Positive and negative charge areas are blue and red, respectively. NAD is shown as yellow sticks. CBP-interacting residues are shown as thin sticks (grey). CBP (orange), HTS11955 (2-(1,3-benzothiazol-2-ylsulfanyl)-N-(3-cyano-6-methyl-4,5,6,7-tetrahydro-1-benzo-thiophen-2-yl)acetamide) (magenta) and RH00573 (2-amino-4-methylsulfanyl-6-[2-(3-nitrophenyl)-2-oxoethyl]sulfanylpyridine-3,5-dicarbonitrile) (cyan) are indicated as sticks. The oxygen, nitrogen, and sulfur atoms are colored in red, blue and orange, respectively
FIG. 5B shows the schematic representation of interactions between inhibitors and the CBP-interacting residues. The color representation of inhibitors is as in FIG. 5A. The interactions of hydrogen bond are shown as dash lines.
Figure 5:
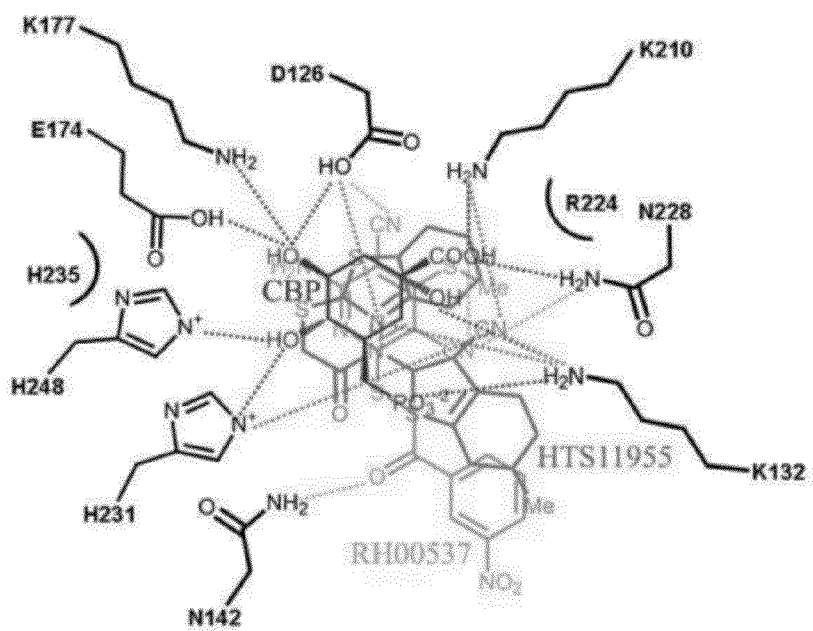

As compared with the substrate analog CBP that contained a single chair-form ring, both inhibitors consisted of two planes that were about 4.5 Å apart. HTS11955 was noted to include two double-ring planes. Like CBP that contained five functional groups (OH, COOH, and phosphate), these compounds carried N or O atoms and a few functional groups (CN, $NH_2$, and $NO_2$) that might hydrogen bond with the nearby residues. Superimposition of these docked models (CBP, HTS11955, and RH00573) showed that these compounds occupy most the CBP site rather than the NAD site (shown as FIG. 5A). One plane from either inhibitor was situated approximately at or near the site of the chair-form ring of CBP. As a result, they made contacts with CBP-interacting residues (63.8 Å), particularly D126, K132, E174, K177, K210, and H231 (shown as FIG. 5B), hence exhibiting their inhibition of DHQS enzymatic activity. These results together suggested a feasible structure-based method for discovering compounds that was able to be utilized to develop potent inhibitors.

In conclusion, the example had determined the 2.4-A HpDHQS•NAD structure, which was of an open form. The conserved dimeric structural feature seen in all DHQS structures was likely to play a vital role in sustaining the fine-tuned design of active sites. Based on the determined structure, virtual computational screening of a diverse set of compounds and inhibition analysis revealed two inhibitors, HTS11955 and RH00573, which served as initial leads. This example demonstrated a feasible structure-based approach to discovering potential inhibitors of DHQS activity.

Protein Data Bank Codes

The atomic coordinates and structural factors for the HpDHQS (PDB code: 3CLH) had been deposited in the Protein Data Bank, Research Collaboratory for Structural Bioinformatics, Rutgers University, New Brunswick, N.J. (http://www.rcsb.org/).

Example 2

Example 2 was the inhibitor screening of shikimate kinase of *H. pylori* and *M. tuberculosis*.

Materials and Methods

Preparations of the Target Proteins and Screening Databases

Two databases were used as follows: about 59284 compounds from the Maybridge chemical database and about 260,071 compounds from the NCI database. Molecule structures of two databases were prepared from ZINC database. The compound set was prepared by selecting them from the databases based on two criteria: (1) molecular weight ranging between 200 and 600, and (2) no compounds with multiple components. A set comprising 50102 and 218703 compounds was eventually obtained from Maybridge and NCI, respectively.

The structures of *H. pylori* shikimate kinase (HpSK, PDB code 1zuh and 1zui) and *M. tuberculosis* shikimate kinase (MtSK, PDB code 2iyt and 1zyu) were aligned by Combinatorial Extension (CE). For identifying inhibitors that are competitive both in ATP and shikimate sites, the structure of the binding pocket in the SKM-ACP bounded conformation (PDB code 1zyu), including amino acids enclosed within a 8 Å radius sphere centered on the bound ligands, was used for virtual screening. The same region was applied for the other structures (1zuh, 1zui and 2iyt). The coordinates of protein atoms were taken from the PDB for the screening processing. All binding pockets on shikimate kinase proteins were isolated and prepared for the GEMDOCK.

Constructing Homologous Pharmacophores

Homologous pharmacophore were the common pharmacophore spots of multiple proteins and represented the conserved binding environment and compound moieties. A compound matched more homologous pharmacophores might have higher probability to be orthologous-target inhibitors Construction of homologous pharmacophore from virtual screening contained six steps as follows:

(1) Selection of the top-ranked compounds fitted in both HpSK and MtSK. The virtual screening of HpSK (1zuh and 1zui) and MtSK (2iyt and 1zyu) were performed by GEMDOCK. GEMDOCK docked each compound of the two databases against the binding pockets, and ranked each compound by its docked energy. To identify compounds fitted both HpSK and MtSK, a procedure of rank fusion was adapted to combine the energy ranks of compounds in the apo forms (1zuh and 2iyt) and the close forms (1zui and 1zyu), respectively. The procedure used a rank-based consensus scoring for re-ranking compounds. The consensus score (CS) of each compound x was defined as $$CS(x) = R_{Ht}(x) + R_{Mt}(x)$$

where $R_{Ht}(x)$ and $R_{Mt}(x)$ were the energy rank of HtSK and MtSK, respectively The top 3000 compounds of rank fusion in each form were chosen for constructing homologous pharmacophores.

(2) Generation of protein-ligand interaction array. Interaction arrays presented the overall protein-ligand interactions of top-ranked compounds in binding sites. Scoring function of GEMDOCK was applied for generating protein-ligand interactions of all docked complexes. The protein-ligand interactions included three types of interactions: electrostatic (E), hydrogen-bonding (H), and van der Waals (vdW) interactions (Step 2 in FIG. 6). The array of each interaction type x was defined as $$a(x) = \begin{bmatrix} a_{1,1} & a_{1,2} & \cdots & a_{1,2K} \\ a_{2,1} & a_{2,2} & \cdots & a_{2,2K} \\ \vdots & \vdots & \ddots & \vdots \\ a_{N,1} & a_{N,2} & \cdots & a_{N,2K} \end{bmatrix}$$

where $a_{i,j}$ was the binary value, N was the number of selected representative compounds, and K was the number of residues. The array length was 2k because interactions of a residue were divided into two types; one type was main chain, and the other type was side chain. The reason was that the major difference between amino acids was the different groups of side chains. In a(E) and a(H), $a_{i,j}$ was set to 1 if the distance of an interaction was less than 3.3 Å. In a(V), $a_{i,j}$ was set to 1 if energy between residues and a compound was less than −8, which was an empirical threshold. In GEMDOCK scoring function, vdW energy of π-π stacking interactions was less than −8.

(3) Determining the selected compounds. The selected compounds (N) must contain two properties: (1) they must contain the diversity of compound structures, and pharmacophore spots were not dominated by the same compound structure. (2) The distribution of shuffled interaction frequency of these compounds was approximated a normal distribution. Consensus interactions with statistical significance could be identified by the normal distribution.

To ensure there was as wide a range of potential scaffolds as possible involved in the sampling of pharmacophore spots, a cluster analysis for compound scaffolds was adapted on the top ranks of screening results. For each group of compounds, a compound with the lowest energy was selected as the representative structure of this group. Structural descriptors of the top-ranked compounds were generated by the atom pair (AP) descriptors. Atom pair descriptors consist of a pair of non-hydrogen atom types and the shortest bond distance between them. All pairs of atoms in the topological representation of a chemical structure were exhaustedly scanned. Finally, a chemical structure of a compound would be described as a vector with 825 accumulated values of types (Atom A—shortest distance—atom B). The AP vector was then transformed as the bit string. If the value on an AP type was over zero, then the bit on the type set as 1. The Tanimoto coefficient (Tc) was adapted as the quantitative measure of bit string similarity. The Tc between two bit strings, A and B, was defined as:

$$Tc(A, B) = \frac{|A \cap B|}{|A \cup B|}$$

where $|A \cap B|$ was the number of ON bits common in both A and B and $|A \cup B|$ as the number of ON bits present in either A or B. A hierarchical clustering methodology was applied to analyze the AP bit strings of top ranks. The AP strings were clustered by using a hierarchical clustering approach, applying the Tanimoto coefficients as similarity measurements. Hierarchical clustering analyses were carried out with MATLAB cluster analysis module.

The statistical Z-score was employed to measure how significant the consensus interactions are. To identify consensus interactions with significance on the binding sites, the interaction frequency of each array was translated into the Z-score profile by the stand deviation and mean of a background set. The interaction frequency of each array (f(x)) was defined as $$f_j = \sum_{i=1}^{N} a_{i,j}/N$$

$$f(x) = [\,f_1 \quad f_2 \quad \cdots \quad f_{2K}\,]$$

where $f_j$ was the interaction frequency of a column. In each array, 2000 random interaction frequency were derived as the background set by shuffling the position of $a_{i,j}$, and the distribution of the interaction frequency was a binomial distribution. Statistically, a binomial distribution was approximated a normal distribution when either $p \leq 0.5$ and $np > 5$ or $p > 0.5$ and $n(1-p) > 5$, where n was the number of trials and p was the probability of success.

In the present invention, N had to satisfy 2 criteria as follows: (1) N had to be larger than the minimal n that satisfied the equation $$np_n > 5 \text{ or } n(1-p_n) > 5$$

in the three arrays, where n was the number of top-ranked representative compounds, and $p_n$ was the interaction occurrence probability of n compounds. (2) N had to be larger than the 1% of the amount of the compound database. In this study, 600 representative compounds were selected for constructing pharmacophore spot model.

Figure 8:
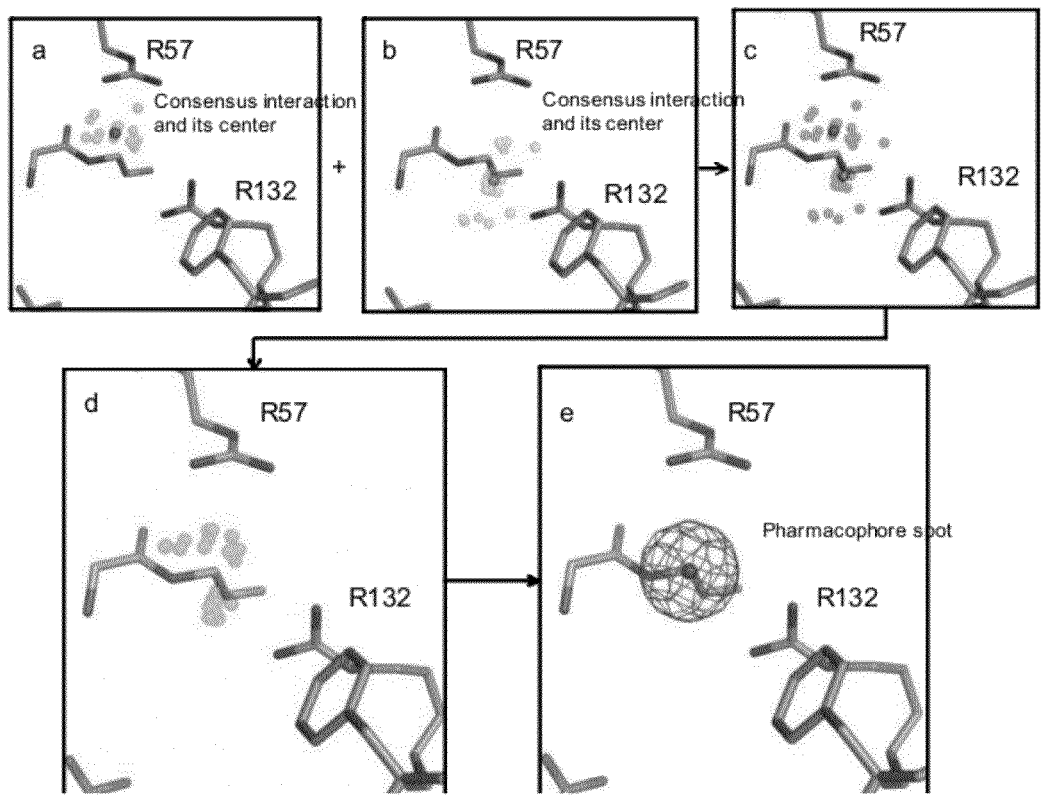
FIG. 8 shows schematic of deriving pharmacophore spots.

(4) Construction of pharmacophore profiles. Pharmacophore profiles were used to identify consensus interactions on the binding sites. The pharmacophore profile of each interaction type x was defined as $$p_j = \frac{f_j - m}{d}$$

$$p(x) = [\,p_1 \quad p_2 \quad \cdots \quad p_{2K}\,]$$

where $p_j$ was the Z-score in column j, and m and d were the frequency mean and stand deviation of the background set, respectively The cutoffs of Z-score used to determine the consensus interactions of electrostatics, hydrogen-bonding, and vdW profiles were 2, 10, and 10, respectively (5) Generation of pharmacophore spots. A pharmacophore spot was a specific region that prefers a set of similar compound moieties having consensus interactions with proteins (Step 3 in FIG. 6). Consensus interactions that were spatially closed and the same type were merged as a spot candidate. The centers of consensus interactions were centers of ligand atoms that have consensus interactions of the same type (FIGS. 8a and 8b). For identifying electrostatic and hydrogen-bonding spots, ligand atoms that had consensus interactions (FIG. 8c) were assigned into multiple centers of consensus interactions if their distances were less than 2.5 Å (FIG. 8d). A pharmacophore spot was the center of these ligand atoms of multiple centers (FIG. 8e).

The definition of vdW spots was different from electrostatic and hydrogen-bonding spots because vdW interactions formed by several residues in a pocket. In this study, the binding sites of HpSK and MtSK were divided into three pockets, triphosphate, shikimate, and adenosine pockets for identifying inhibitors that were competitive both in ATP and shikimate sites. The residues that ever had consensus interactions were listed as follows: (1) In the triphosphate pocket, they were M10, G11, G13, K14, and E114 of HpSK (P11, G12, G14, K15, and T115 of MtSK). (2) In the shikimate pocket, they were M10, F48, and G80 of HtSK (P11, F49, and G80 of MtSK). (3) In adenosine pocket, it of R107 in HtSK (R110 in MtSK). vdW consensus interactions were classified to the three pockets, and the vdW pharmacophore spot of each pocket was the centers of consensus interaction centers.

The pharmacophore score of a compound was the sum of the matched pharmacophore spots. The pharmacophore spot model consisted of the three types (vdW, electrostatic, hydrogen bonding) of pharmacophore spots in the binding site (Step 4 in FIG. 6).

(6) Generation of homologous pharmacophores. Homologous pharmacophores were the common pharmacophore spots of multiple proteins and represent the conserved binding environment and compound moieties. The definition of common spots was that the distance between either two spot centers of two proteins was less than 2.5 Å. A compound matched more homologous pharmacophores might have higher probability to be a orthologous-target inhibitors. A homologous pharmacophore score was used to measure how well a compound fit the homologous pharmacophores of HpSK and MtSK. The weight of each spot was defined as $$\text{Weight} = \frac{NC}{NA}$$

where NC as the number of proteins having the homologous pharmacophore, and NA was the number of aligned proteins. In this study, the aligned proteins were apo and closed forms of HtSK and MtSK, and NA was 4. For example, the weight of hot spot E1 was 1, and the weight of spot E2 was 0.25 because only apo form of HtSK had the pharmacophore spot. Hot spots with high weights indicated that they were essential to inhibit orthologous targets. A homologous pharmacophore score of a compound was the sum of the weighted pharmacophore spot scores in apo forms of HpSK and MtSK.

Enzyme Activity Assay

The shikimate kinase activity was determined by coupling the release of ADP from the shikimate kinase-catalyzed reaction to the oxidation of NADH using pyruvate kinase (EC 2.7.1.40) and lactate dehydrogenase (EC 1.1.1.27) as coupling enzymes. Shikimate-dependent oxidation of NADH was monitored by the decrease in A340 ($\epsilon = 6{,}200\ M^{-1}\ cm^{-1}$).

The assay was carried out at 25° C. in a mixture containing 100 mM Tris/HCl/KOH buffer, pH 7.5, 50 mM KCl, 5 mM MgCl$_2$, 1.6 mM shikimic acid, 2.5 mM ATP, 1 mM phosphoenolpyruvate, 0.1 mM NADH, 2.5 units of pyruvate kinase/ml, and 2.7 units of lactate dehydrogenase/ml. All assays were conducted in a 96-well microplate spectrophotometer (FLUOstar OPTIMA, BMG LABTECH). Kinetic parameters were obtained using nonlinear regression fitting to the Michaelis-Menten equation. The apparent Km values for each substrate were determined as follows: for ATP the shikimate concentration ([shikimate]) was maintained at 1.6 mM and the [ATP] varied in the range from 0.001 mM to 2.5 mM; for shikimate the [ATP] was maintained at 2.5 mM and the [shikimate] varied in the range from 0.005 to 1.6 mM. The kinetic data were fit to the appropriate equations using the program GraphPad Prism 4 (Software Inc., USA). The kinetic data for determining the Km values were fit to $$v = \frac{V_{max}[S]}{K_m + [S]}$$

using the program GraphPad Prism 4 where v was the initial velocity, $V_{max}$ was the maximum velocity, Km was the Michaelis constant and [S] was the substrate (shikimate or ATP) concentration. The IC$_{50}$ value for HpSK inhibition by inhibitors was determined by fitting data to $$v = V_{min} + \frac{V_{max} - V_{min}}{1 + \left(\frac{[I]}{IC_{50}}\right)^n}$$

where v was the initial velocity, $V_{max}$ was the maximum velocity, $V_{min}$ was the minimum velocity, [I] was the concentration of compounds and n was the Hill slope.

Inhibitor Activity Assay

Using GEMDOCK virtual docking and pharmarcophore model, several compounds were selected to assay inhibitor activity for verifying the inhibiting effect on HpSK and MtSK enzyme. Based on the procedure of enzyme activity assay, the initial velocities of the enzyme activity were determined in the presence of compounds (50 μM) dissolved in dimethylsulfoxide (DMSO). The final DMSO concentration in all assay mixtures was 5% (v/v). The assay buffer contained 100 mM Tris/HCl/KOH (pH 7.5), 1.6 mM shikimic acid, 2.5 mM ATP. The reaction was initiated by the addition of the diluted HpSK and MtSK enzyme (85 nM). After the preliminary screening, several compounds were identified to inhibit HpSK and MtSK enzyme activity. The initial velocities of the enzyme activity were determined in the presence of various concentrations of these compounds to investigate the dose-dependent inhibition effects. IC50 values of these compounds were obtained by fitting the data to a sigmoid dose-response equation of the GraphPad Prism 4. Afterwards, inhibitor modality was determined by measuring the effects of inhibitor concentrations on the enzymatic activity as a function of substrate concentration. In the inhibition experiment where the ATP concentration was fixed at 2.5 mM, shikimate was a varied substrate (0.06, 0.12, 0.24, 0.48, and 0.96 mM) when the concentration of inhibitor was varied from 0 to 50 μM. In parallel, in the inhibition experiment where the shikimate concentration was fixed at 1.6 mM, ATP was a varied substrate (0.06, 0.12, 0.24, 0.48, and 0.96 mM) when the concentration of inhibitor was varied from 0 to 50 μM.

Results

Development of the Homologous Pharmacophore Method

Figure 6:
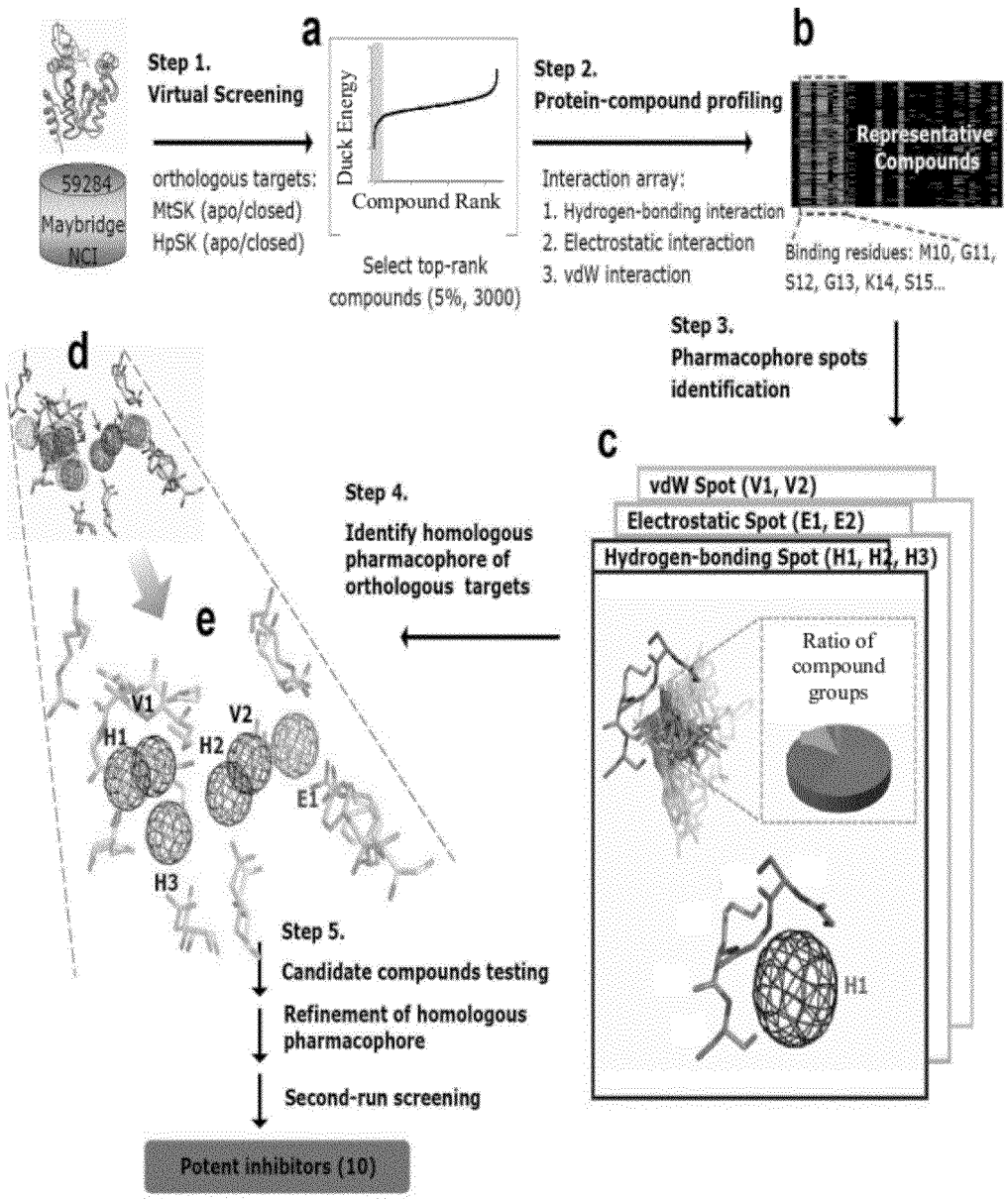
FIG. 6 shows pharmacophore spots of HpSK and MtSK from virtual screening. In Step 1, GEMDOCK was used to generate docked poses for HpSK and MtSK by screening compound libraries (Maybridge and NCI). In Step 2, for each target, the protein-compound interacting profile was derived from fusing top rank 3000 compounds of HpSK and MtSK. In Step 3, conserved interactions and combinatory moieties are identified to infer the pharmacophore spots of HpSK and MtSK. In Stpe 4, the homologous pharmacophores are constructed using orthologous-target pharmacophores and are used to selected candidates compounds for bioassay Finally, the homologous pharmacophores are refined based on bioassay of candidate compounds.

A homologous pharmacophore was defined as a molecular framework that consisted of a set of consensus pharmacophore spots between orthologous proteins to ensure their conserved binding environments. The following criteria were considered: (1) targets were orthologous proteins; (2) the structural binding sites of orthologous targets shared conserved features; (3) the derived pharmacophores from orthologous targets shared comparable spots with respect to their sites and crucial protein-ligand interactions. FIG. 6 illustrated the major steps of this method.

1. Virtual screening of orthologous targets over public compound libraries. The present invention utilized home-made GEMDOCK program to screen Maybridge (50,102 compounds) and NCI (218,703 compounds) databases against both HpSK (apo/closed form) and MtSK (apo/closed form). The ligand ranks of each target were combined by rank fusion and 5% (~3,000 compounds) (FIG. 6a) of fused top ranks were selected from screening results to proceed subsequent protein-compound profiling.

2. Profiling analysis of target-compound interactions among top-ranking compounds. Here, target-compound interactions of top-ranking compounds (15%) were assessed to derive a few candidate "spots" enclosing a subset of specific amino acids poised in an environment to accommodate related chemical entities (FIG. 6b). The present invention therefore referred it as a bonding environment or a pharmacophore spot. Three types of pharmacophore spots were considered based on protein-compound interactions: hydrogen-bonding (H), electrostatic (E) and van der Waals (V) interactions (FIG. 6b). The selected compounds should keep the diversity of compound structures and the target-compound interacting profile was approximated a normal distribution. The size of protein-ligand interaction array was 3×M×N where M and N represented the numbers of selected compounds and interacting residues of the target, respectively. The interacting force was increasing as the color from dark to green.

Figure 9:
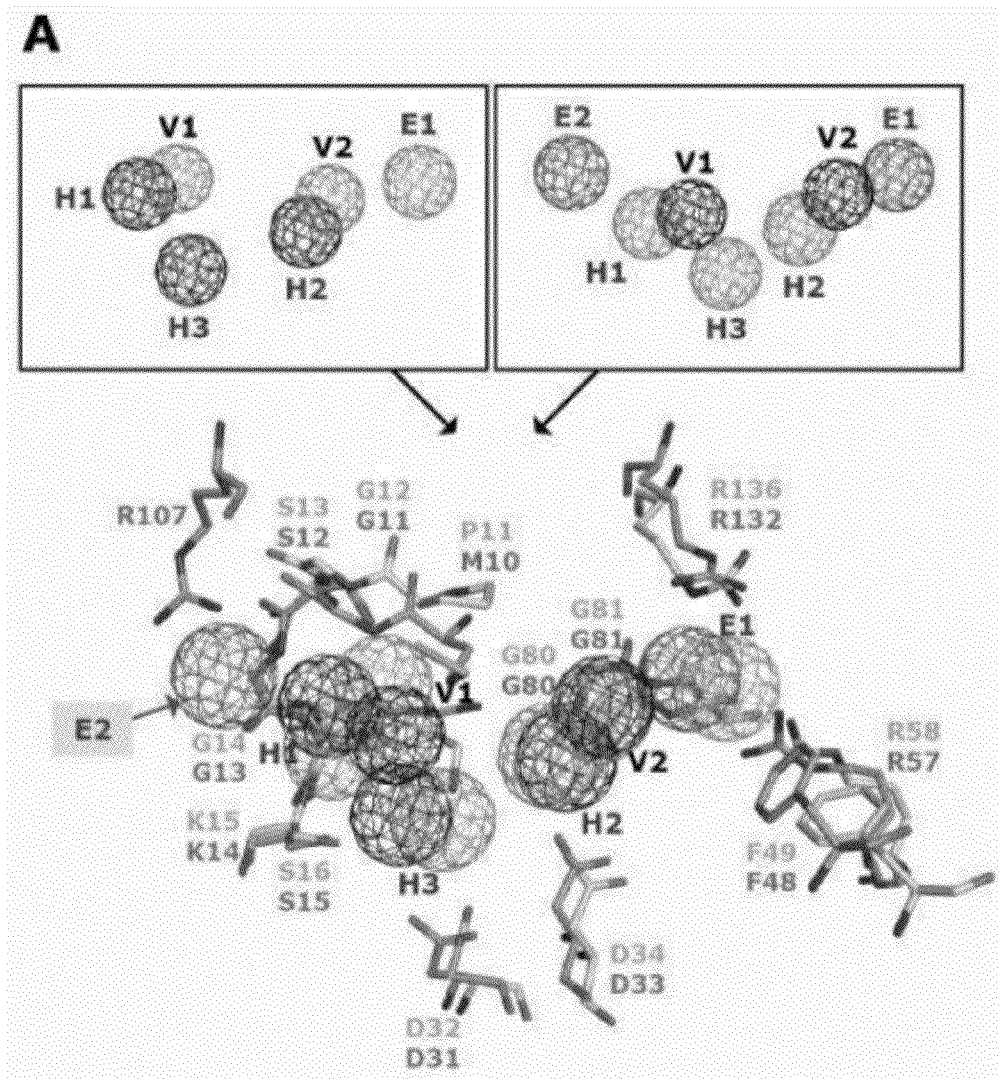
FIG. 9 shows the conserved pharmacophore spots and aligned spots of (A) apo forms and (B) close forms. The HpSK and MtSK share 6 and 4 pharmacophore hot spots, respectively, for (C) apo and (D) close forms. The conserved pharmacophore spots of apo form and close form of shikimate kinase are four spots, including H1, V1, H2, and E1. The consensus functional groups and interacting residues for targets HpSK and MtSK are considered as pharmacophore hot spots.
Figure 10A:
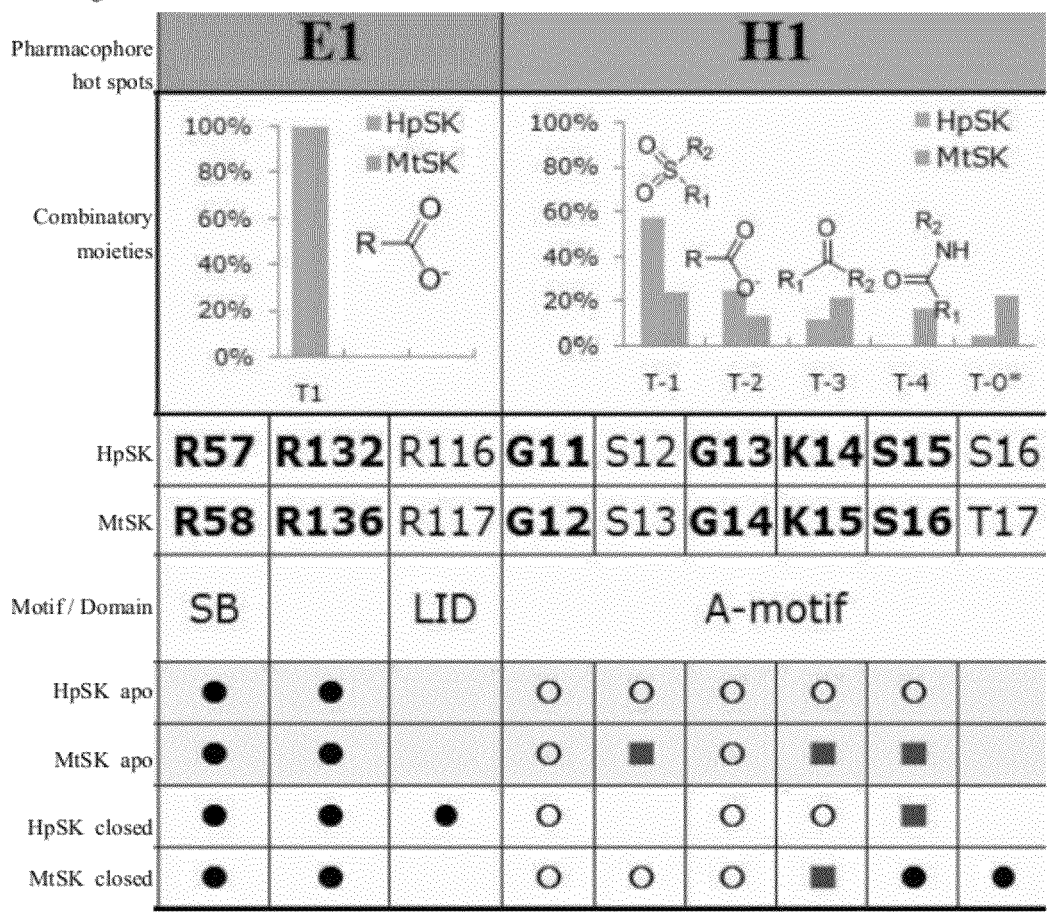
FIG. 10 shows conserved pharmacophore spots and their functional groups. Six pharmacophore hot spots are located in ATP (H1, V1, and H3) and shikimate (H2,V2, and E1) sites. Each pharmacophore hot spot consists of conserved interacting residues and functional groups of compound candidates. The conserved residue interactions can be divided into side-chain (•), backbone (○), and both (■).
Figure 10B:
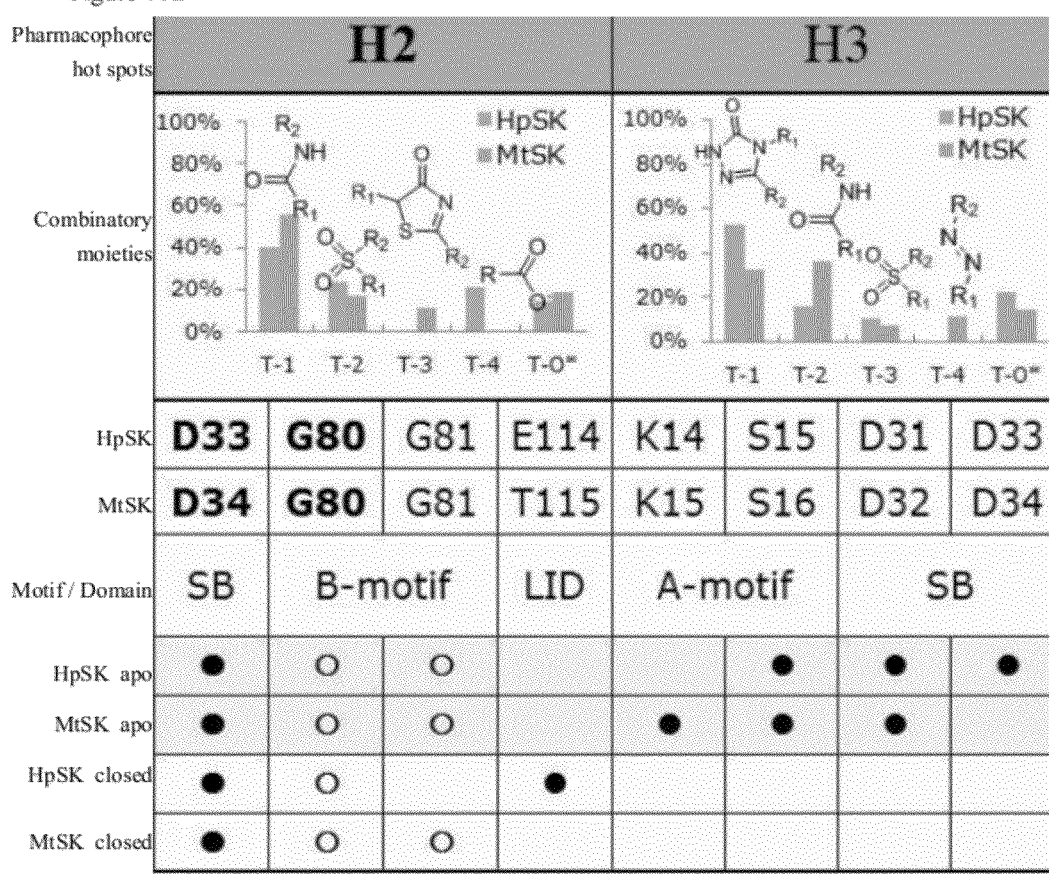
Figure 10C:
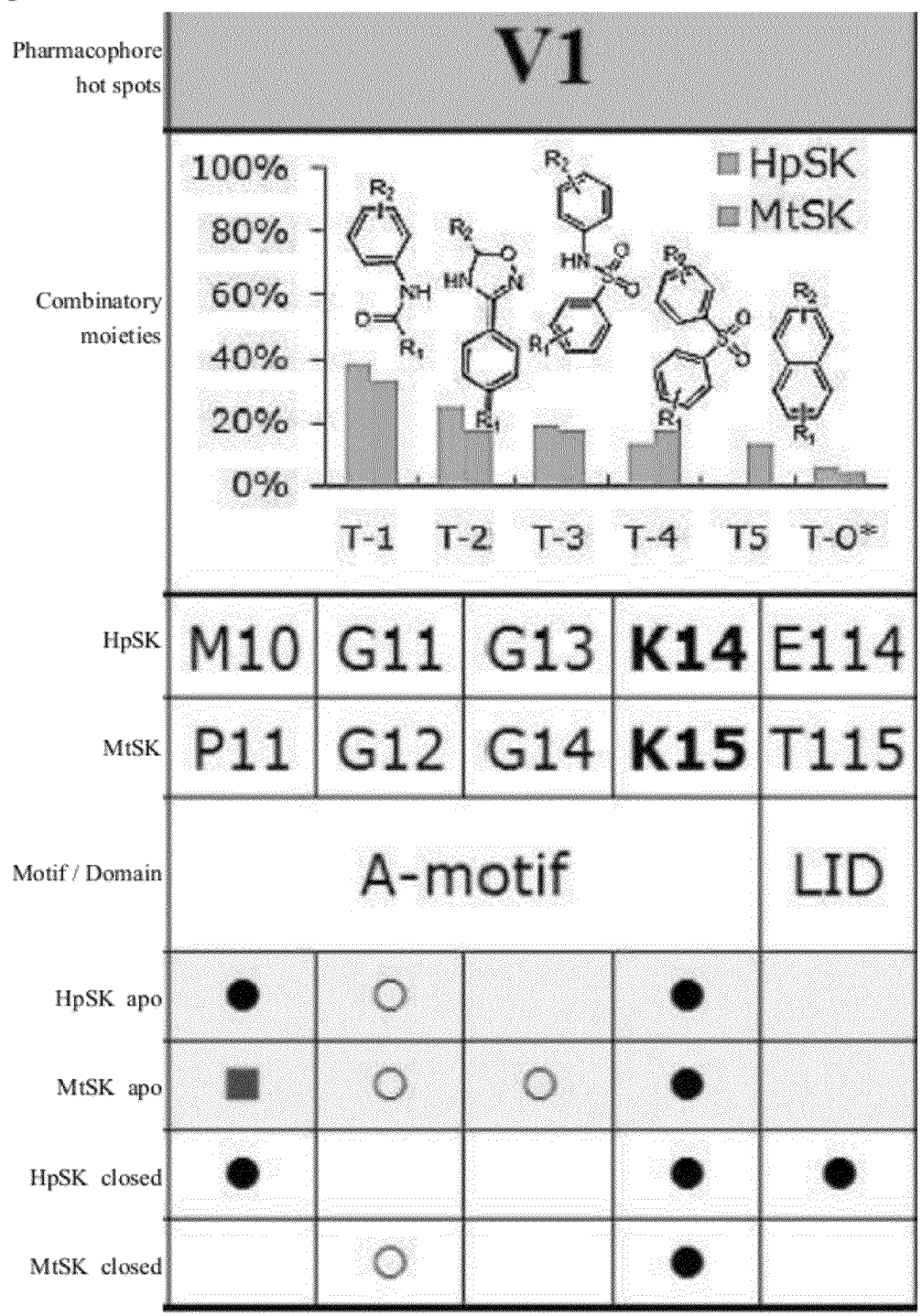
Figure 10D:
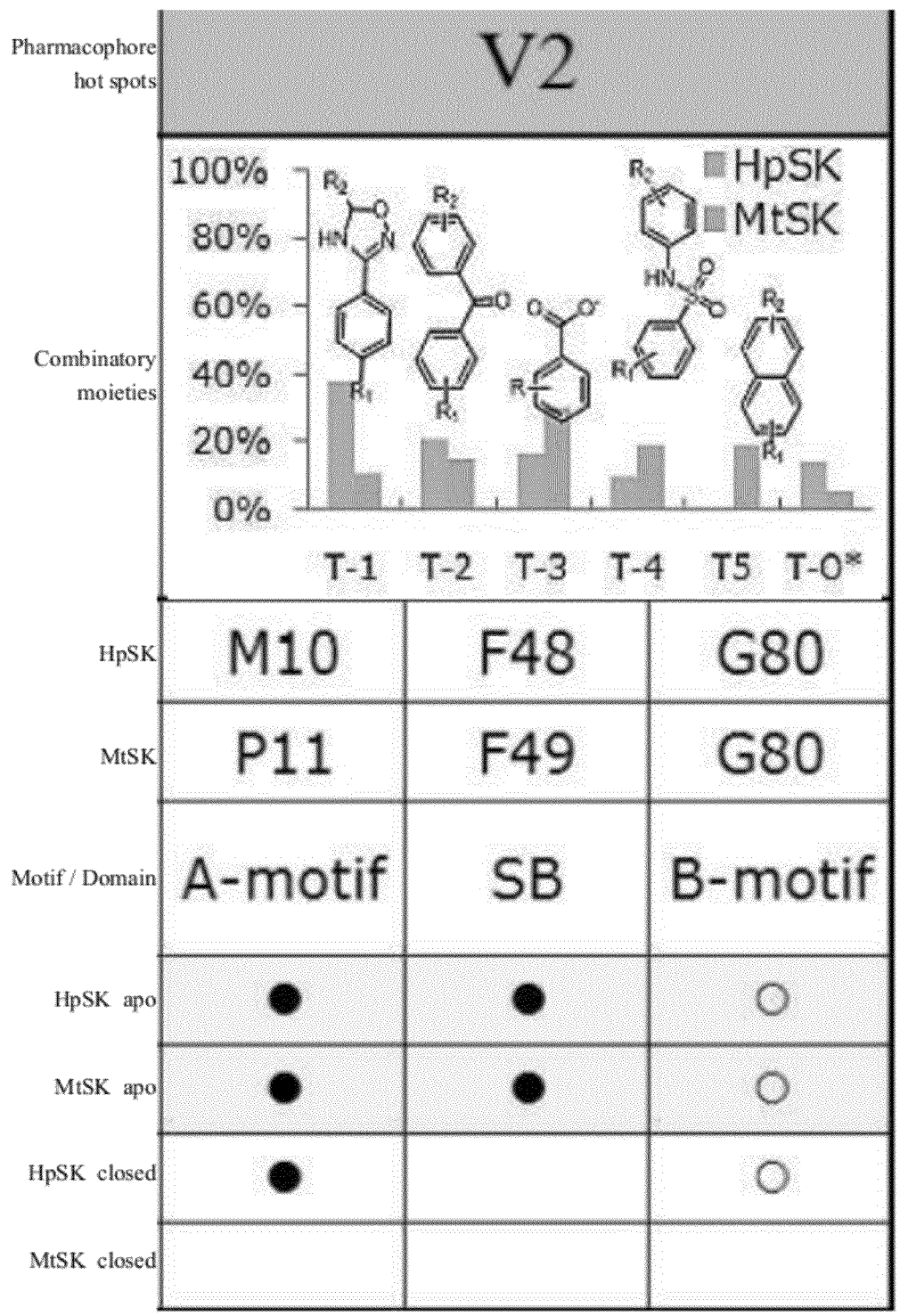

3. Identification of pharmacophore spots and establishment of models. A site having consensus bonding environment with a statistically significant Z-score was referred as a "spot" (FIG. 6c). A set of spots from the derived target-compounds interacting profile in (2) could then be respectively identified to establish a pharmacophore model of each orthologous target (HpSK/MtSK) (FIGS. 6d, 9a, and 9b). For each spot, crucial residues that contributed to this environment as well as those chemical moieties fitted at this site are thereafter identified.

Figure 7:
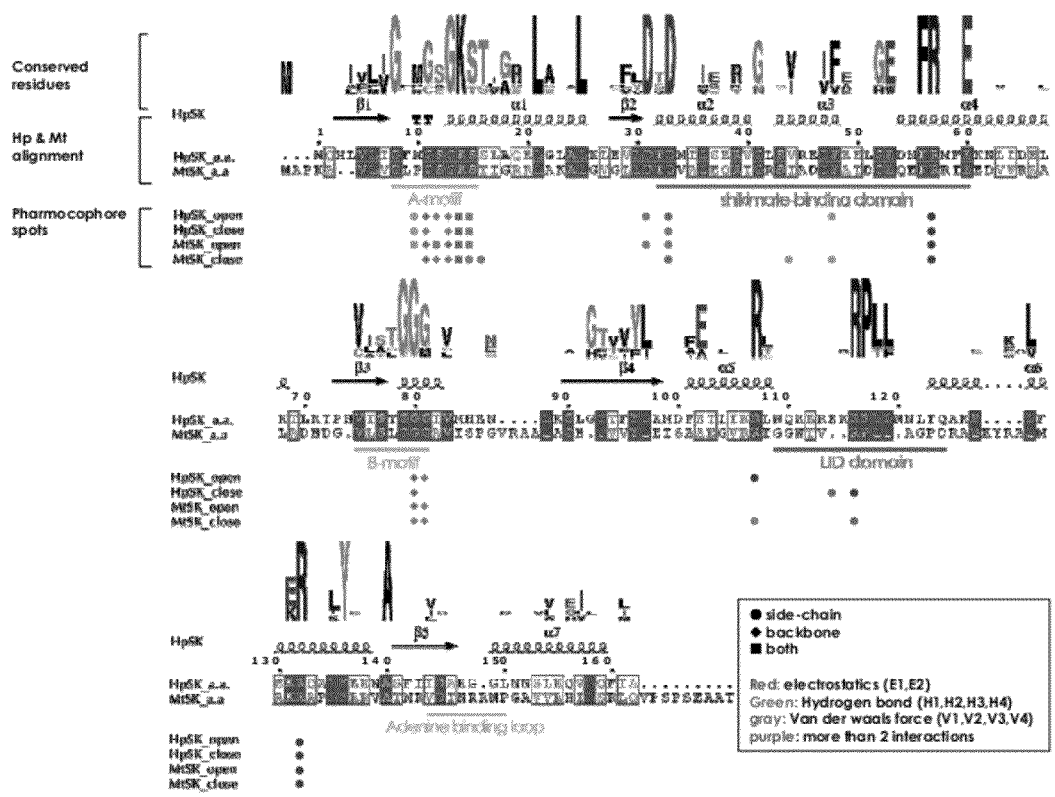
FIG. 7 shows relations of conserved residues, motifs, domains, and pharmacophore hot spots.

4. Establishment of the homologous pharmacophore between orthologous targets (FIG. 7). A consensus spot of the superimposed pharmacophore models (spots) between orthologous proteins (HPSK and MtSK) was considered as a pharmacophore "hot spot". The criteria for a given hot spot were that the superimposed spots of orthologous proteins belonged to the same type and the distances between spot centers were less than 2.5 Å. The homologous pharmacophore, which consisted of a set of hot spots from orthologous targets (FIGS. 6e, 9c, and 9d), reflecting the consensus interactions between conserved binding residues of proteins and functional moieties of compounds. Hot spots thus heavily depended on chemical-physical properties and sculpted the binding sites of targets. The top-ranking compounds were then re-scored using both energy-based and the homologous pharmacophore methods.

5. Inhibition assay of top-ranking compounds. Compounds having the highest scores from the score fitness function based on the apo-form and closed homologous pharmacophore models, respectively were tested for inhibitory assay. The present invention had also chosen 54 compounds that had lower energy scores using energy-based scoring function 6. Refinement of the homologous pharmacophore of orthologous targets. Active and inactive compounds from enzyme inhibition assay were used to evaluate the performance of the homologous pharmacophore model and to refine its hot spots. This model was presumed to enrich the screening hit rate for orthologous targets from public compound libraries.

Establishment of the Homologous Pharmacophore Model between MtSK and HpSK

Homologous pharmacophores that shared comparable spots or "hot spots" between homologous pharmacophores were referred to belong to a pharmacophore family, a scenario analogous to the protein sequence family and protein structure family; the former described the co-evolution between proteins and their interacting partner and the latter described the protein evolution alone. The notion of homologous pharmacophores was considered to be useful in diverse biological investigations. Here, the present invention developed homologous pharmacophores to identify novel inhibitors of shikimate kinases.

Here, a pharmacophore spot was an interacting environment that prefers a set of similar compound moieties consistently interact with a binding subsite (s) on the target. A consensus interacting environment, spatially closed with the same interacting type, was significantly different from other environments to be a spot candidate derived from target-compounds interacting profiles (FIG. 6b). In general, the number of spots of a pharmacophore, derived from known inhibitors for a target protein, was three. Conversely, a pharmacophore, derived from thousand of compounds by screening on given orthologous-based targets, consisted of 6 spots on average. For example, the apo-form pharmacophore (FIG. 9a) of HpSK and MtSK was found to have 6 and 7 spots, respectively Structures of MtSK structures in apo and various liganded forms suggested an open-to-closed conformational change upon ligand binding. Despite low sequence identity (30%), structures of the unliganded and shikimate-binding complex structures also showed an open and closed conformation, respectively Importantly, HpSK and MtSK shared essentially conserved shikimate- and nucleotide-binding residues.

Given the distinctive binding pockets with or without ligands, the present invention sought to establish apo-form and closed-form homologous pharmacophores of shikimate kinase, respectively by use the approach described above (FIG. 6). After virtual screening and profiling analysis, three types of spots (electrostatic, hydrogen bonding, and vdW spot types) in each pharmacophore were identified. For the apo-form pharmacophore, there were 6 (E1, H1, H2, H3, V1, and V2) and 7 (E1, E2, H1, H2, H3, V1, and V2) spots for MtSK and HpSK (FIG. 9a), respectively. The close-form pharmacophore, on the other hand, consisted of 7 (E1, H1, H2, H4, V1, V3, and V4) and 5 (E1, H1, H2, V1, and V2) spots for MtSK and HpSK (FIG. 9b), respectively.

The present invention next identified the consensus spots of orthologous proteins as the hot spots that form the homologous pharmacophore and represented the conserved interacting environments for each form. The apo-form homologous pharmacophore possessed 6 (E1, H1, H2, H3, V1, and V2) (FIG. 9c). Contrarily, there were only 4 (E1, H1, H2, and V1) hot spots for the close-form pharmacophore (FIG. 9d), revealing a less consensus environment, these four hot spots were noted to exist in the apo-form model.

Each hot spot of a homologous pharmacophore possessed a consensus interacting environment which consisted of both conserved interacting residues and functional groups (FIG. 10). In general, a hot spot contained a set of chemotypes, interacting to conserved binding subsite among orthologous targets, for guiding the combinatorial library design for further compound development and lead optimization. The apo-form and close-form hot spots of HpSK and MtSK were different on hot spots H3 and V2, which were absence in the closed form. Six hot spots, derived from MtSK apo form of HpSK and MtSK, are summarized as follows:

The hot spot E1 contained the negative charge pocket with R57 (R58 in MtSK) and R132 (R136 in MtSK) which were highly conserved for shikimate kinase and participated in the binding of shikimate acid. The consensus functional groups on E1 were carboxyl, sulfonate, and phosphate, and phosphonate. The compositions of these groups on HpSK were carboxyl (64%), sulfonate (29%), and phosphate (4%). On MtSK, the percentages were carboxyl (68%), sulfonate (30%) and phosphonate (2%).

For spot V2, this hot spot was identified on the borders of both shikimate and ATP binding domains. The V2 included the interacting subsite of target proteins (F48, G80, and M10 for HpSK and F49, G80, and P11 for HPSK) and the functional groups are tolyl-oxadiazole, tolylmethanone and benzoate groups (FIG. 10). For HpSK, the compositions of these groups were 38%, 21% and 17%, respectively. For MtSK, the compositions were 11%, 15% and 30%, respectively.

The hot spot H2 was formed between the subsite, the shikimate binding domain and B-Motif, of targets and the functional groups (amide, sulfone and thiazolone) of compounds. These groups consistently interacted to the hydroxyl group of shikimate acid, which was the key point of phosphoryl transfer reaction, and are amide (40% for HpSK and 56% for MtSK) and sulfon (23% for HpSK and 17% for MtSK) (FIG. 10). The spot H3 was much closed to the location of the metal ion, $Mg^{2+}$ which was participated in the catalytic reaction of phosphoryl transfer. The hydrogen bonding interactions of H3 were formed by the contribution of side-chains of conserved residues, D31 and D33 and A-motif (K14 and S15) on HpSK, and functional groups (triazolone, amide, and sulfone) of accommodated compounds. The compositions of these groups for HpSK were 52%, 16% and 10%, respectively.

Hot spots, H1 and V1, were located on the binding pocket of beta/gamma phosphate groups of ATP. The spot Hi was a hydrogen-bonding environment involving between a subsite (the phosphate binding site and A-motif) of targets and a set of functional groups of compounds for forming hydrogen bonds. The A-motif was a conserved sequence which forms a loop for accommodating the phosphate groups of substrate. The functional groups of H1 consisted of sulfone (58% for HpSK and 24% for MtSK), carboxyl (25% for HpSK and 14% for MtSK), and ketone (12% for HpSK and 22% for MtSK) groups. The spot V1, vdW environment, was contributed between the residues, which were M10, G11, G13, and K14 (P11, G12, G14, K15 of MtSK), and the functional groups (tolyacetamide, tolyl-oxadiazole and tolylbenzenesulfonamide groups) of compounds. The compositions of these functional groups on HpSK were 38% (tolyacetamide), 25% (tolyl-oxadiazole), and 19% (tolylbenzenesulfonamide).

Inhibition Assay of Top-Ranking Hits

Figure 11:
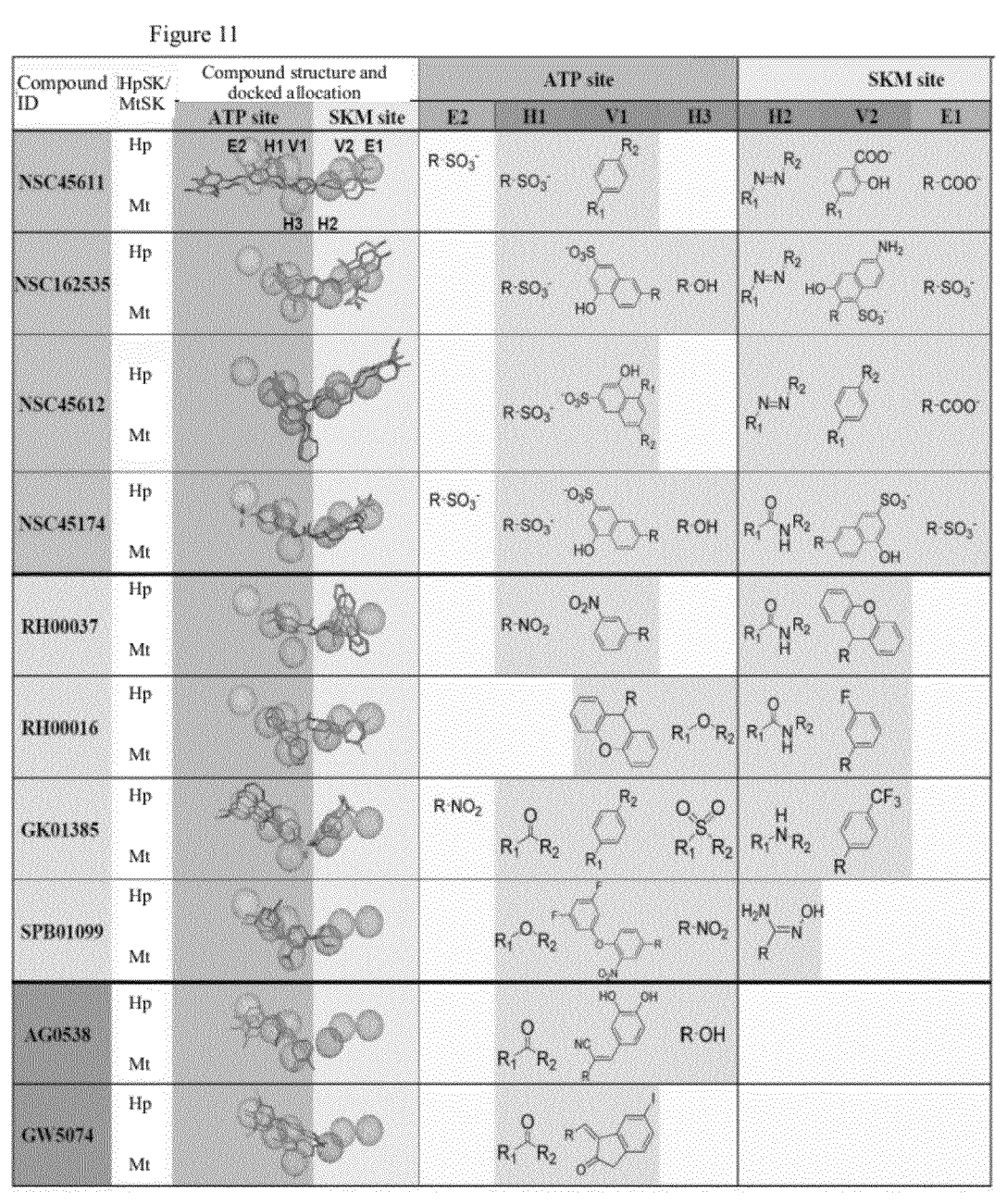

The top-ranking compounds that were commercially available were then purchased for inhibitory assay. Of 46 from the apo-form model using energy-based and pharmacophore-based scores by screening both Maybridge and NCI databases, 8 had an IC50 value $\leq 100$ μM for both HpSK and MtSK (FIG. 11). Four (NSC45611, NSC162535, NSC45612, and NSC45174) compounds, selected from NCI database among these 8compounds, demonstrated IC50 values of $\leq 10$ μM. On the other hand, 46 compounds from the close-form model none had detectable inhibitory activity. In parallel, 40 existing kinase inhibitors were tested to evaluate their inhibitory effects against shikimate kinase. Of these, two, AG538 and GW5074, showed inhibitory results.

Eight active compounds matched the homologous pharmacophore hot spots on both ATP and SKM sites (FIG. 11). The docked poses of four NCI compounds consistently occupied the spots E1, V2, H2, H3, V1, and H1. The inhibition assay showed that three NCI compounds were competitive on both two sites except NSC45174. For four Maybridge compounds, they had no negatively charged chemotypes to form electrostatic interactions with R57 and R132 in HtSK (R58 and R136 in MtSK) on the hot spot E1 (FIG. 10). The spot E1 was critical for inhibiting the shikimare kinases and might explain that the IC50 values of NCI compounds were lower than that of Maybridge compounds. Conversely, the docked poses of two kinase compounds located and matched the hot spots on ATP site. The bioassay showed that they were competitive for ATP and noncompetitive for shikimate (FIG. 11).

The function groups of active compounds matched the moiety compositions of homologous pharmacophore spots of HpSK and MtSK (FIG. 11). The interacting functional groups of NSC1 62535, NSC45612, and NSC45174 on H1 were the sulfonate substitution which had 58% and 24% in the combinatory moieties of H1 in HpSK and MtSK, respectively. In E1, NCI compounds were all satisfied with the negative charged demand by sulfonate or carboxyl groups which were 100% of carboxyl group from screening compounds. In H2, NSC45611, NSC162535, and NSC45612 were satisfied the requirement of hydrogen-bonding interactions on this pocket via diazene moiety which was 6% for MtSK. In V2, NSC45174 and NSC162535 had the naphthanlene scaffold which was 19% for MtSK. NSC45611 and NSC45612 had the benzene scaffold which was 17% and 30% for HpSK and MtSK, respectively. The vdW scaffold of NSC162535, NSC45612, and NSC45174 on the hot spot V1was the chemotype of naphthanlen, which was 13% for MtSK. The Hydroxyl group on H3 spot took 5% and 2% in the HpSK and MtSK, respectively.

The average molecular weights of selected compounds using apo and closed form were 393.6 and 289.7 Dalton, respectively, and the average numbers of hydrogen bonding acceptors of selected compounds by apo and closed form were 8.0 and 6.1, respectively For the closed-form shikimate structures of HpSK and MtSK, the compounds with large vdW contact moieties, benzoate or benzophenone scaffolds, could not be docked into the SKM binding pocket, therefore, the V2 was not formed in the closed-form homologous pharmacophore.

The developed structure-based strategy here had identified 10 new chemical entities that were active against both the wild-type strain.

The inhibition modes of inhibitors that had IC50 $\leq$μM including compounds 5-8 and AG538 were first determined with respect to ATP. In the presence of increasing fixed concentrations of an inhibitor and saturated concentration of shikimate, the HpSK or MtSK activity was detected at various concentrations of ATP, followed by the Lineweaver-Burk analysis. The lines at various fixed concentrations of AG538 intersected at the 1/V axis with respect to ATP, confirming that AG538 was an ATP analogue. For compounds 5-8, the double-reciprocal plot also showed that the lines of each compound intersect at the 1/V axis (data not shown). These results suggested that all inhibitors were competitive inhibitors. The present invention next evaluated the inhibition mode with respect to shikimate. For AG538, the lines at various fixed concentrations of AG538 intersected at the 1/shikimate axis, indicating a noncompetitive mode. Compound 5 also demonstrated a noncompetitive inhibition, whereas compounds 6-8 fitted into a competitive inhibition. Importantly, HpSK and MtSK showed the same inhibitory patterns for all inhibitors. Table 2 summarized IC50 values and the kinetic data of compounds 1-8, AG538, and GW5074.

Performance of Homologous Pharmacophore of Orthologous Targets

Figure 12:
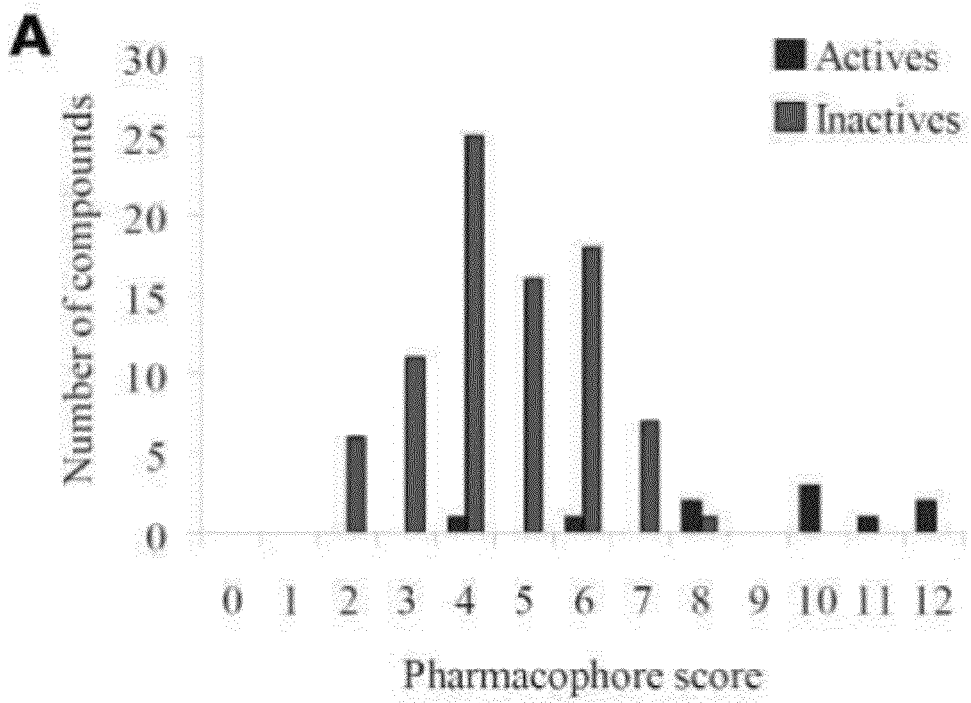
FIG. 12 shows performance of pharmacophore hot spots and multiple-target design. For 94 bioassay compounds (10 active compound and 84 inactive compounds) for HpSK and MtSK, (A) the pharmacophore score is able to discriminate the active (blue) and inactive (red) compounds except two kinase compounds; conversely, (B) the energy score is unable to discriminate active and inactive compounds. Based on the true hit, the pharmacophore scores (solid line) significantly outperforms energy-based scores (dash line) for (A) 94 bioassay compounds and (B) top ranked 2000 compound in Maybridge database.
Figure 12:
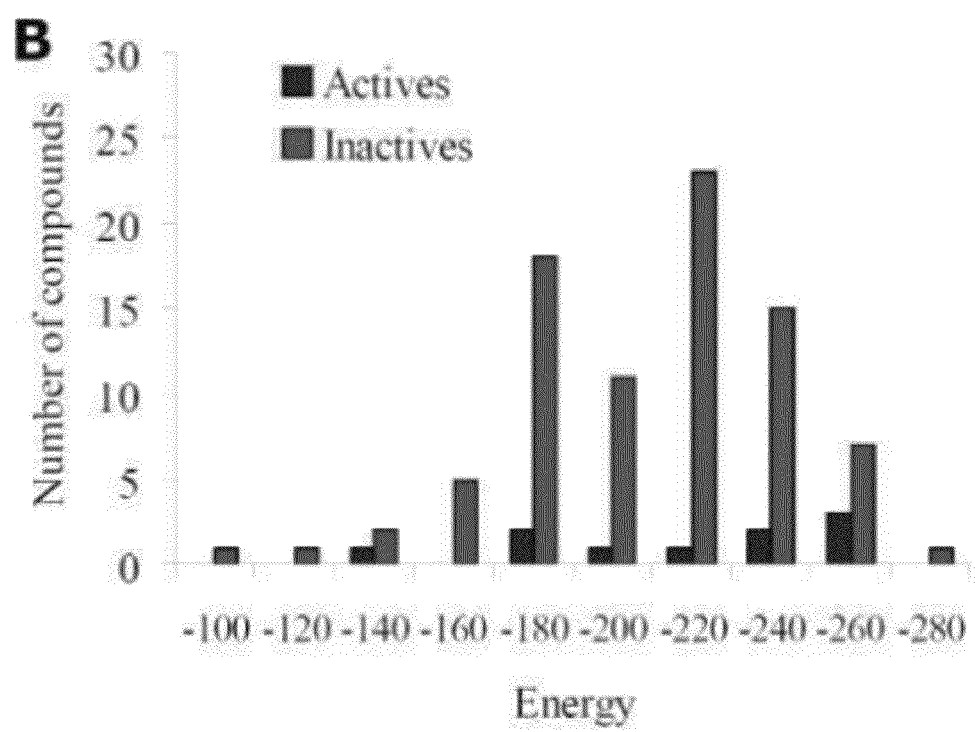

The pharmacophore scores significantly outperformed energy-based scores for identifying novel inhibitors for HpSK and MtSK by screening from Maybridge and NCI databases (FIG. 12a and Table 1). The performances of the pharmacophore-based scoring methods were better than that of the energy-based scoring methods, and the homologous pharmacophore from orthologous targets had the best performance. Here, the present invention used the hit rate and the enrichment for evaluating the overall quality (and performance) of a scoring method. The hit rate was defined $A_h/T_h$ (%) and $(A_h/T_h)/(A/T)$ was the enrichment, where $A_h$ was the number of active bioassay compounds among the $T_h$ highest ranking compounds (i.e., the hit list), A was the total number of active ligands in the database, and T was the total number of compounds in the database. Here, the $A_h$ was 8 based on bioassay results and T was 6000 based on fusing top-ranked 6000 compounds from screening databases.

The homologous pharmacophore from orthologous targets (HPSK and MtSK) was superior to the comparative approaches and the individual pharmacophore score (HPSK or MtSK) was better than energy-based scoring methods, widely used in docking tools (FIG. 12a and Table 2). For example, the average hit rates were 0.92% (HpSK), 0.21% (MtSK), and 0.37% (Fusion HpSK and MtSK) using energy-based scoring methods. The hit rates were improved to 34.13% (HpSK), 17.57% (MtSK), and 67.02% (Fusion HpSK and MtSK) using pharmacophore scoring methods. The average enrichment were 6.91 (HpSK), 1.58 (MtSK), and 2.74 (Fusion HpSK and MtSK) using energy-based scoring methods. When homologous pharmacophore score was carried out, the enrichment improved from 2.74 to 504.02.

TABLE 2

Summary of 8 active compounds included compound structures and ranks of energy-based and pharmacophore-based scores using top-rank 6000 compounds by fusing Maybridge and NCI databases

| Compound ID | Compound structure | Energy rank | | |
|---|---|---|---|---|
| | | HpSK | MtSK | Hp + Mt |
| NSC45611 | | 1761 | 1591 | 1546 |
| NSC162535 | | 1789 | 201 | 456 |
| NSC45612 | | 26 | 2779 | 217 |
| NSC45174 | | 82 | 1356 | 229 |
| RH00037 | | 3017 | 3253 | 3441 |
| RH00016 | | 6001 | 5883 | 6008 |

TABLE 2-continued

GK01385 — [structure drawn] — 2429  1877  2166

SPB01099 — [structure drawn] — 4704  5189  5062

| Compound ID | Pharmacophore rank | | |
|---|---|---|---|
| | HpSK | MtSK | Hp + Mt |
| NSC45611 | 4 | 61 | 3 |
| NSC162535 | 5 | 2 | 2 |
| NSC45612 | 9 | 84 | 4 |
| NSC45174 | 1 | 3 | 1 |
| RH00037 | 474 | 641 | 44 |
| RH00016 | 84 | 115 | 10 |
| GK01385 | 58 | 70 | 9 |
| SPB01099 | 608 | 835 | 130 |

Among 94 bioassay compounds, the homologous pharmacophore was able to discriminate the active (10) and inactive (84) compounds for HpSK and MtSK except two kinase compounds (FIG. 12b). In contrast, the energy-based scoring methods were unable to discriminate these compounds. 4 among 10 active compounds were identified from Maybridge database and the highest pharmacophore score was 8.5. Conversely, the highest pharmacophore score of 4 NCI active compounds was 11 and their IC50 was much better than those selected from Maybridge database (FIG. 11). Among 84 inactive compounds, 38 and 46 compounds were obtained from apo and close forms, respectively.

The homologous pharmacophore reduced the deleterious effects of screening ligand structures that were rich in charged or polar atoms. Most energy-based scoring functions favored the selection of high molecular weight compounds, which often had high vdW potential and high polar compounds (due to hydrogen-bonding and electrostatic potentials), and considered all interactions as the same even when some interactions were essential to chemical reactions. For example, a compound (ZINC code 06002217), of which molecular weight and number of polar atoms are 572.6 and 17, respectively, was the third rank using the energy-based scoring method in the top-ranked 6000 compounds. In contrast, the rank of this compound was 3991 according to the scores of homologous pharmacophore because it matched few pharmacophore hot spots.

Two top-ranked 100 compounds selected by using the homologous pharmacophore and the energy-based scoring methods, respectively, were selected as the pharmacophore set and the energy set. The average molecular weights of the pharmacophore set and the energy set were 488.0 and 534.8, respectively, and the average numbers of polar atoms were 11.9 (pharmacophore set) and 14.2 (energy set). These results showed that the homologous pharmacophore achieved a fairly significant improvement (vs. energy-based scoring methods) in several measures of scoring quality, specifically, hit rate and enrichment.

Example 1 was the inhibitor screening of HpDHQS, consequently, chemical compound HTS11955 and RH00573 were the screened inhibitors of HpDHQS (shown in Table 1). The steps of inhibitor screening of shikimate kinase was shown in Example 2, wherein the inhibitor candidates were GK01385, RH00037, RH00016, SPB01099, NSC45174, NSC45611, NSC45612, NSC162535, AG538, (IGF-1 receptor kinase inhibitor) and GW5074 (shown in Table 1). The inhibition data of the inhibitors against HpSK and MtSK were shown in Table 3.

TABLE 3

Kinetic inhibition data of the inhibitors against HpSK and MtSK

| Cpds | SKM | ATP | IC50 (μM) | αKi, SKM (μM) | αKi, ATP (μM) |
|---|---|---|---|---|---|
| HpSK | | | | | |
| 1 | — | — | 79.29 | — | — |
| 2 | — | — | 23.82 | — | — |
| 3 | — | — | 40.23 | — | — |
| 4 | — | — | 89.84 | — | — |
| 5 | Noncompetitive | Competitive | 7.77 | 12.80 | 1.74 |
| 6 | Competitive | Competitive | 4.78 | 1.73 | 1.05 |
| 7 | Competitive | Competitive | 6.10 | 2.42 | 1.97 |
| 8 | Competitive | Competitive | 4.91 | 1.82 | 1.85 |
| 9 | Noncompetitive | Competitive | 2.30 | 5.35 | 3.08 |
| 10 | — | — | 31.40 | — | — |
| MtSK | | | | | |
| 1 | — | — | >50 | — | — |
| 2 | — | — | >50 | — | — |
| 3 | — | — | >50 | — | — |
| 4 | — | — | >50 | — | — |
| 5 | Noncompetitive | Competitive | 2.76 | 2.67 | 0.35 |
| 6 | Competitive | Competitive | 1.50 | 0.66 | 0.32 |
| 7 | Competitive | Competitive | 2.77 | 1.04 | 0.73 |
| 8 | Competitive | Competitive | 1.55 | 0.61 | 0.24 |
| 9 | Noncompetitive | Competitive | 0.37 | 0.38 | 0.038 |
| 10 | — | — | 29.58 | | |

Compounds 1 to 10 were: 1. GK01385, 2. RH00037, 3. RH00016, 4. SPB01099, 5. NSC45174, 6. NSC45611, 7. NSC45612, 8. NSC136535, 9. AG538, and 10. GW5074.

Based on pharmacophore model, 92 compounds were selected to test the inhibiting effect. Ten compounds were discovered as HpSK and MtSK inhibitors. The inhibitor mode was also determined. The data collected at varied shikimate (or ATP) and inhibitor concentrations yielded a series of intersecting lines when plotted as a double-reciprocal plot. Kinetic analysis indicated that NSC45174 and AG538 were noncompetitive inhibitors with respect to shikimate as fitted to the noncompetitive inhibition equation:

$$v = \frac{v\max[S]}{[S]\left(1 + \frac{[I]}{\alpha Ki}\right) + Km\left(1 + \frac{[I]}{Ki}\right)}$$

where Ki was the dissociation constant for the inhibitor-enzyme complex, and αKi was the dissociation constant for the inhibitor-enzyme-substrate complex. NSC45611, NSC45612 and NSC136535 acted as a competitive inhibitor with respect to shikimate fitting to the competitive inhibition equation:

$$v = \frac{V\max[S]}{[S] + Km\left(1 + \frac{[I]}{Ki}\right)}$$

On the other hand, all compounds were competitive inhibitors with respect to ATP. Table 3 summarized the $IC_{50}$ values and kinetic inhibition data.

One skilled in the art readily appreciates that the present invention is well adapted to carry out the objects and obtain the ends and advantages mentioned, as well as those inherent therein. The processes and methods used herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of identifying a drug candidate to a target protein for inhibiting shikimate pathway, comprising
    (a) performing a molecular docking program, GEM-DOCK, for computing a molecule conformation and orientation relative to an active site of the target protein and selecting top-rank molecules by docked energy of docked poses generated by the program,
    (b) generating protein-molecule interacting profiles, which comprises three interaction types (x), hydrogen-bonding interactions (H), electrostatic interactions (E) and VDW interactions (V), of the molecules selected from step (a) and identifying conserved interactions and pharmacophore spots,
        wherein the protein-molecule interacting profile of each interaction type x is defined as $$a(x) = \begin{bmatrix} a_{1,1} & a_{1,2} & \cdots & a_{1,2K} \\ a_{2,1} & a_{2,2} & \cdots & a_{2,2K} \\ \vdots & \vdots & \ddots & \vdots \\ a_{N,1} & a_{N,2} & \cdots & a_{N,2K} \end{bmatrix}$$

wherein $a_{i,j}$ is a binary value, N is a number of molecules selected from step (a), and K is a number of residues; and
        steps for identifying conserved interactions are as follows:
        (i) calculating interaction frequency of each protein-molecule interacting profile which is defined as $$f_j = \sum_{i=1}^{N} a_{i,j}/N$$

$$f(x) = [f_1 f_2 \cdots f_{2K}]$$

wherein $f_j$ is the interaction frequency of a column,
        (ii) constructing a pharmacophore profile which is defined as $$p_j = \frac{f_j - m}{d}$$

$$p(x) = [p_1 \; p_2 \; \cdots \; p_{2K}]$$

wherein $p_j$ is Z-score in column j, and m is frequency mean of a background set, and d is stand deviation of the background set,
            wherein a cutoff of the Z-score used to identify the conserved interactions of electrostatics, hydrogen-bonding, and VDW profile is set to 1.645, and
        steps for identifying pharmacophore spots (electrostatic and hydrogen-bonding) are as follows:
        (iii) merging conserved interactions that are spatially closed and the same type as a spot candidate,
        (iv) assigning atoms of molecules selected from step (a) that have conserved interactions into multiple centers of conserved interactions if their distances were less than 2.5 Å,
        (v) identifying pharmacophore spot as center of molecular atoms assigned to multiple centers, and steps for identifying pharmacophore spots (VDW) are as follows:
        (vi) dividing binding sites of the target protein into different pockets,
        (vii) listing out amino acids had conserved interactions of each pocket,
        (viii) identifying pharmacophore spot as the center of conserved interaction centers,
    (c) developing homologous pharmacophore models from the interacting profiles of step (b) for identifying pharmacophore hot spots by superimposing multiple pharmacophore spots of homologues of the target proteins,
        wherein the superimposed pharmacophore spots of the homologues of the target proteins are defined as pharmacophore hot spots if they have (1) distance less than 2.5Å, and (2) same interaction type,
        wherein, a weight of a pharmacophore hot spot is defined as $$\text{Weight} = \frac{NC}{NA}$$

wherein NC is a number of proteins having the homologous pharmacophore, and NA is a number of aligned proteins, and
    (d) rescoring molecules selected from step (a) by their homologous pharmacophore scores,
        wherein the homologous pharmacophore score of a molecule is obtained by following steps:
        (ix) calculating a pharmacophore scores for each pharmacophore hot spot,
            wherein, the pharmacophore score of a molecule is set to 1 if the molecule matched the pharmacophore hot spot; otherwise, the the score is set to 0,
        (x) calculating a weighted pharmacophore score for each pharmacophore hot spot,
            wherein the weighted pharmacophore score is obtained by multiplying the pharmacophore score by the weight derived from step (c),
        (xi) calculating a homologous pharmacophore score of the molecule by summing the weighted pharmacophore score in apo forms of the target protein, and (e) selecting potential molecules which have the highest homologous pharmacophore scores based on the apo-form and closed homologous pharmacophore models, and (f) acquiring corresponding real compounds of the potential molecules selected from step (e) and identifying their inhibitory activity on the target protein by bioassay.

2. The method of claim 1, wherein the bioassay of step (f) is enzyme activity assay.

3. The method of claim 1, which further comprises a step (g) after step (f), wherein the step (g) is to evaluate performance of the homologous pharmacophore models of step (c) using active and inactive molecules from bioasssay of step (f), and refine hot spots of the homologous pharmacophore models.

* * * * *

SEQUENCE LISTING

<160> NUMBER OF SEQ ID NOS: 6

<210> SEQ ID NO 1
<211> LENGTH: 343
<212> TYPE: PRT
<213> ORGANISM: Helicobacter pylori
<220> FEATURE:
<221> NAME/KEY: ACT_SITE
<222> LOCATION: (1)..(343)

<400> SEQUENCE: 1

```
Met Gln Glu Ile Leu Ile Pro Leu Lys Glu Lys Asn Tyr Lys Val Phe
1               5                   10                  15

Leu Gly Glu Leu Pro Glu Ile Lys Leu Lys Gln Lys Ala Leu Ile Ile
            20                  25                  30

Ser Asp Ser Ile Val Ala Gly Leu His Leu Pro Tyr Leu Leu Glu Arg
        35                  40                  45

Leu Lys Ala Leu Glu Val Arg Val Cys Val Ile Glu Ser Gly Glu Lys
    50                  55                  60

Tyr Lys Asn Phe His Ser Leu Glu Arg Ile Leu Asn Asn Ala Phe Glu
65                  70                  75                  80

Met Gln Leu Asn Arg His Ser Leu Met Ile Ala Leu Gly Gly Gly Val
                85                  90                  95

Ile Ser Asp Met Val Gly Phe Ala Ser Ser Ile Tyr Phe Arg Gly Ile
            100                 105                 110

Asp Phe Ile Asn Ile Pro Thr Thr Leu Leu Ala Gln Val Asp Ala Ser
        115                 120                 125

Val Gly Gly Lys Thr Gly Ile Asn Thr Pro Tyr Gly Lys Asn Leu Thr
    130                 135                 140

Gly Ser Phe His Gln Pro Lys Ala Val Tyr Met Asp Leu Ala Phe Leu
145                 150                 155                 160

Lys Thr Leu Glu Lys Arg Glu Phe Gln Ala Gly Val Ala Glu Ile Ile
                165                 170                 175

Lys Met Ala Val Cys Phe Asp Lys Asn Leu Val Glu Arg Leu Glu Thr
            180                 185                 190

Lys Asp Leu Lys Asp Cys Leu Glu Glu Val Ile Phe Gln Ser Val Asn
        195                 200                 205

Ile Lys Ala Gln Val Val Gln Asp Glu Lys Glu Gln Asn Ile Arg
    210                 215                 220

Ala Gly Leu Asn Tyr Gly His Thr Phe Gly His Ala Ile Glu Lys Glu
225                 230                 235                 240

Thr Asp Tyr Glu Arg Phe Leu His Gly Glu Ala Ile Ala Ile Gly Met
                245                 250                 255

Arg Met Ala Asn Asp Leu Ala Leu Ser Leu Gly Met Leu Thr Leu Lys
            260                 265                 270

Glu Tyr Glu Arg Ile Glu Asn Leu Leu Lys Lys Phe Asp Leu Ile Phe
        275                 280                 285

His Tyr Lys Ile Leu Asp Leu Gln Lys Phe Tyr Glu Arg Leu Phe Leu
    290                 295                 300

Asp Lys Lys Ser Glu Asn Lys Thr Ile Lys Phe Ile Leu Pro Lys Gly
305                 310                 315                 320

Val Gly Ala Phe Glu Val Ala Ser His Ile Pro Lys Glu Thr Ile Ile
                325                 330                 335

Lys Val Leu Glu Lys Trp His
            340
```

<210> SEQ ID NO 2
<211> LENGTH: 393
<212> TYPE: PRT
<213> ORGANISM: Aspegillus nidulans
<220> FEATURE:
<221> NAME/KEY: ACT_SITE
<222> LOCATION: (1)..(393)

<400> SEQUENCE: 2

Met Ser Asn Pro Thr Lys Ile Ser Ile Leu Gly Arg Glu Ser Ile Ile
1               5                   10                  15

Ala Asp Phe Gly Leu Trp Arg Asn Tyr Val Ala Lys Asp Leu Ile Ser
            20                  25                  30

Asp Cys Ser Ser Thr Thr Tyr Val Leu Val Thr Asp Thr Asn Ile Gly
        35                  40                  45

Ser Ile Tyr Thr Pro Ser Phe Glu Glu Ala Phe Arg Lys Ala Ala Ala
    50                  55                  60

Glu Ile Thr Pro Ser Pro Arg Leu Leu Ile Tyr Asn Arg Pro Pro Gly
65                  70                  75                  80

Glu Val Ser Lys Ser Arg Gln Thr Lys Ala Asp Ile Glu Asp Trp Met
                85                  90                  95

Leu Ser Gln Asn Pro Pro Cys Gly Arg Asp Thr Val Val Ile Ala Leu
            100                 105                 110

Gly Gly Gly Val Ile Gly Asp Leu Thr Gly Phe Val Ala Ser Thr Tyr
        115                 120                 125

Met Arg Gly Val Arg Tyr Val Gln Val Pro Thr Thr Leu Leu Ala Met
    130                 135                 140

Val Asp Ser Ser Ile Gly Gly Lys Thr Ala Ile Asp Thr Pro Leu Gly
145                 150                 155                 160

Lys Asn Leu Ile Gly Ala Ile Trp Gln Pro Thr Lys Ile Tyr Ile Asp
                165                 170                 175

Leu Glu Phe Leu Glu Thr Leu Pro Val Arg Glu Phe Ile Asn Gly Met
            180                 185                 190

Ala Glu Val Ile Lys Thr Ala Ala Ile Ser Ser Glu Glu Glu Phe Thr
        195                 200                 205

Ala Leu Glu Glu Asn Ala Glu Thr Ile Leu Lys Ala Val Arg Arg Glu
    210                 215                 220

Val Thr Pro Gly Glu His Arg Phe Glu Gly Thr Glu Glu Ile Leu Lys
225                 230                 235                 240

Ala Arg Ile Leu Ala Ser Ala Arg His Lys Ala Tyr Val Val Ser Ala
                245                 250                 255

Asp Glu Arg Glu Gly Gly Leu Arg Asn Leu Leu Asn Trp Gly His Ser
            260                 265                 270

Ile Gly His Ala Ile Glu Ala Ile Leu Thr Pro Gln Ile Leu His Gly
        275                 280                 285

Glu Cys Val Ala Ile Gly Met Val Lys Glu Ala Glu Leu Ala Arg His
    290                 295                 300

Leu Gly Ile Leu Lys Gly Val Ala Val Ser Arg Ile Val Lys Cys Leu
305                 310                 315                 320

Ala Ala Tyr Gly Leu Pro Thr Ser Leu Lys Asp Ala Arg Ile Arg Lys
                325                 330                 335

Leu Thr Ala Gly Lys His Cys Ser Val Asp Gln Leu Met Phe Asn Met
            340                 345                 350

Ala Leu Asp Lys Lys Asn Asp Gly Pro Lys Lys Ile Val Leu Leu
        355                 360                 365

```
Ser Ala Ile Gly Thr Pro Tyr Glu Thr Arg Ala Ser Val Val Ala Asn
    370                 375                 380

Glu Asp Ile Arg Val Val Leu Ala Pro
385                 390

<210> SEQ ID NO 3
<211> LENGTH: 354
<212> TYPE: PRT
<213> ORGANISM: Staphylococcus aureus
<220> FEATURE:
<221> NAME/KEY: ACT_SITE
<222> LOCATION: (1)..(354)

<400> SEQUENCE: 3

Met Lys Leu Gln Thr Thr Tyr Pro Ser Asn Asn Tyr Pro Ile Tyr Val
1               5                   10                  15

Glu His Gly Ala Ile Lys Tyr Ile Gly Thr Tyr Leu Asn Gln Phe Asp
            20                  25                  30

Gln Ser Phe Leu Leu Ile Asp Glu Tyr Val Asn Gln Tyr Phe Ala Asn
        35                  40                  45

Lys Phe Asp Asp Ile Leu Ser Tyr Glu Asn Val His Lys Val Ile Ile
50                  55                  60

Pro Ala Gly Glu Lys Thr Lys Thr Phe Glu Gln Tyr Gln Glu Thr Leu
65                  70                  75                  80

Glu Tyr Ile Leu Ser His His Val Thr Arg Asn Thr Ala Ile Ile Ala
                85                  90                  95

Val Gly Gly Gly Ala Thr Gly Asp Phe Ala Gly Phe Val Ala Ala Thr
            100                 105                 110

Leu Leu Arg Gly Val His Phe Ile Gln Val Pro Thr Thr Ile Leu Ala
        115                 120                 125

His Asp Ser Ser Val Gly Gly Lys Val Gly Ile Asn Ser Lys Gln Gly
130                 135                 140

Lys Asn Leu Ile Gly Ala Phe Tyr Arg Pro Thr Ala Val Ile Tyr Asp
145                 150                 155                 160

Leu Asp Phe Leu Lys Thr Leu Pro Phe Lys Gln Ile Leu Ser Gly Tyr
                165                 170                 175

Ala Glu Val Tyr Lys His Ala Leu Leu Asn Gly Glu Ser Ala Thr Gln
            180                 185                 190

Asp Ile Glu Gln His Phe Lys Asp Arg Glu Ile Leu Gln Ser Leu Asn
        195                 200                 205

Gly Met Asp Lys Tyr Ile Ala Lys Gly Ile Glu Thr Lys Leu Asp Ile
210                 215                 220

Val Val Ala Asp Glu Lys Glu Gln Gly Val Arg Lys Phe Leu Asn Leu
225                 230                 235                 240

Gly His Thr Phe Gly His Ala Val Glu Tyr Tyr His Lys Ile Pro His
                245                 250                 255

Gly His Ala Val Met Val Gly Ile Ile Tyr Gln Phe Ile Val Ala Asn
            260                 265                 270

Ala Leu Phe Asp Ser Lys His Asp Ile Ser His Tyr Ile Gln Tyr Leu
        275                 280                 285

Ile Gln Leu Gly Tyr Pro Leu Asp Met Ile Thr Asp Leu Asp Phe Glu
290                 295                 300

Thr Leu Tyr Gln Tyr Met Leu Ser Asp Lys Lys Asn Asp Lys Gln Gly
305                 310                 315                 320

Val Gln Met Val Leu Met Arg Gln Phe Gly Asp Ile Val Val Gln His
                325                 330                 335
```

```
Val Asp Gln Leu Thr Leu Gln His Ala Cys Glu Gln Leu Lys Thr Tyr
            340                 345                 350

Phe Lys

<210> SEQ ID NO 4
<211> LENGTH: 348
<212> TYPE: PRT
<213> ORGANISM: Thermus thermophilus
<220> FEATURE:
<221> NAME/KEY: ACT_SITE
<222> LOCATION: (1)..(348)

<400> SEQUENCE: 4

Met Gln Arg Leu Glu Val Arg Glu Pro Val Pro Tyr Pro Ile Leu Val
1               5                   10                  15

Gly Glu Gly Val Leu Lys Glu Val Pro Pro Leu Ala Gly Pro Ala Ala
            20                  25                  30

Leu Leu Phe Asp Arg Arg Val Glu Gly Phe Ala Gln Glu Val Ala Lys
        35                  40                  45

Ala Leu Gly Val Arg His Leu Leu Gly Leu Pro Gly Gly Glu Ala Ala
    50                  55                  60

Lys Ser Leu Glu Val Tyr Gly Lys Val Leu Ser Trp Leu Ala Glu Lys
65                  70                  75                  80

Gly Leu Pro Arg Asn Ala Thr Leu Leu Val Gly Gly Thr Leu
                85                  90                  95

Thr Asp Leu Gly Gly Phe Val Ala Ala Thr Tyr Leu Arg Gly Val Ala
            100                 105                 110

Tyr Leu Ala Phe Pro Thr Thr Thr Leu Ala Ile Val Asp Ala Ser Val
        115                 120                 125

Gly Gly Lys Thr Gly Ile Asn Leu Pro Glu Gly Lys Asn Leu Val Gly
    130                 135                 140

Ala Phe His Phe Pro Gln Gly Val Tyr Ala Glu Leu Arg Ala Leu Lys
145                 150                 155                 160

Thr Leu Pro Leu Pro Thr Phe Lys Glu Gly Leu Val Glu Ala Phe Lys
                165                 170                 175

His Gly Leu Ile Ala Gly Asp Glu Ala Leu Leu Lys Val Glu Asp Leu
            180                 185                 190

Thr Pro Gln Ser Pro Arg Leu Glu Ala Phe Leu Ala Arg Ala Val Ala
        195                 200                 205

Val Lys Val Arg Val Thr Glu Glu Asp Pro Leu Glu Lys Gly Lys Arg
    210                 215                 220

Arg Leu Leu Asn Leu Gly His Thr Leu Gly His Ala Leu Glu Ala Gln
225                 230                 235                 240

Thr Arg His Ala Leu Pro His Gly Met Ala Val Ala Tyr Gly Leu Leu
                245                 250                 255

Tyr Ala Ala Leu Leu Gly Arg Ala Leu Gly Gly Glu Asp Leu Leu Pro
            260                 265                 270

Pro Val Arg Arg Leu Leu Leu Trp Leu Ser Pro Pro Leu Pro Pro
        275                 280                 285

Leu Ala Phe Glu Asp Leu Leu Pro Tyr Leu Leu Arg Asp Lys Lys Lys
    290                 295                 300

Val Ser Glu Ser Leu His Trp Val Pro Leu Ala Pro Gly Arg Leu
305                 310                 315                 320

Val Val Arg Pro Leu Pro Glu Gly Leu Leu Arg Glu Ala Phe Ala Ala
                325                 330                 335
```

```
Trp Arg Glu Glu Leu Lys Gly Leu Gly Leu Leu Arg
            340                 345

<210> SEQ ID NO 5
<211> LENGTH: 162
<212> TYPE: PRT
<213> ORGANISM: Helicobacter pylori
<220> FEATURE:
<221> NAME/KEY: ACT_SITE
<222> LOCATION: (1)..(162)

<400> SEQUENCE: 5

Met Gln His Leu Val Leu Ile Gly Phe Met Gly Ser Gly Lys Ser Ser
1               5                   10                  15

Leu Ala Gln Glu Leu Gly Leu Ala Leu Lys Leu Glu Val Leu Asp Thr
            20                  25                  30

Asp Met Ile Ile Ser Glu Arg Val Gly Leu Ser Val Arg Glu Ile Phe
        35                  40                  45

Glu Glu Leu Gly Glu Asp Asn Phe Arg Met Phe Glu Lys Asn Leu Ile
    50                  55                  60

Asp Glu Leu Lys Thr Leu Lys Thr Pro His Val Ile Ser Thr Gly Gly
65                  70                  75                  80

Gly Ile Val Met His Glu Asn Leu Lys Gly Leu Gly Thr Thr Phe Tyr
                85                  90                  95

Leu Lys Met Asp Phe Glu Thr Leu Ile Lys Arg Leu Asn Gln Lys Glu
            100                 105                 110

Arg Glu Lys Arg Pro Leu Leu Asn Asn Leu Thr Gln Ala Lys Glu Leu
        115                 120                 125

Phe Glu Lys Arg Gln Ala Leu Tyr Glu Lys Asn Ala Ser Phe Ile Ile
    130                 135                 140

Asp Ala Arg Gly Gly Leu Asn Asn Ser Leu Lys Gln Val Leu Gln Phe
145                 150                 155                 160

Ile Ala

<210> SEQ ID NO 6
<211> LENGTH: 176
<212> TYPE: PRT
<213> ORGANISM: Mycobacterium tuberculosis
<220> FEATURE:
<221> NAME/KEY: ACT_SITE
<222> LOCATION: (1)..(176)

<400> SEQUENCE: 6

Met Ala Pro Lys Ala Val Leu Val Gly Leu Pro Gly Ser Gly Lys Ser
1               5                   10                  15

Thr Ile Gly Arg Arg Leu Ala Lys Ala Leu Gly Val Gly Leu Leu Asp
            20                  25                  30

Thr Asp Val Ala Ile Glu Gln Arg Thr Gly Arg Ser Ile Ala Asp Ile
        35                  40                  45

Phe Ala Thr Asp Gly Glu Gln Glu Phe Arg Arg Ile Glu Glu Asp Val
    50                  55                  60

Val Arg Ala Ala Leu Ala Asp His Asp Gly Val Leu Ser Leu Gly Gly
65                  70                  75                  80

Gly Ala Val Thr Ser Pro Gly Val Arg Ala Ala Leu Ala Gly His Thr
                85                  90                  95

Val Val Tyr Leu Glu Ile Ser Ala Ala Glu Gly Val Arg Arg Thr Gly
            100                 105                 110

Gly Asn Thr Val Arg Pro Leu Leu Ala Gly Pro Asp Arg Ala Glu Lys
        115                 120                 125
```

```
Tyr Arg Ala Leu Met Ala Lys Arg Ala Pro Leu Tyr Arg Arg Val Ala
        130             135             140

Thr Met Arg Val Asp Thr Asn Arg Arg Asn Pro Gly Ala Val Val Arg
145             150             155             160

His Ile Leu Ser Arg Leu Gln Val Pro Ser Pro Ser Glu Ala Ala Thr
                165             170             175
```